(12) United States Patent
Wang et al.

(10) Patent No.: US 11,335,465 B2
(45) Date of Patent: May 17, 2022

(54) INFORMATION OUTPUT APPARATUS, INFORMATION OUTPUT METHOD, AND INFORMATION OUTPUT PROGRAM

(71) Applicant: FUJIFILM Corporation, Tokyo (JP)

(72) Inventors: Caihua Wang, Tokyo (JP); Keigo Nakamura, Tokyo (JP)

(73) Assignee: FUJIFILM Corporation, Tokyo (JP)

(*) Notice: Subject to any disclaimer, the term of this patent is extended or adjusted under 35 U.S.C. 154(b) by 44 days.

(21) Appl. No.: 16/786,977

(22) Filed: Feb. 10, 2020

(65) Prior Publication Data
US 2020/0176120 A1 Jun. 4, 2020

Related U.S. Application Data

(63) Continuation of application No. PCT/JP2018/021236, filed on Jun. 1, 2018.

(30) Foreign Application Priority Data

Aug. 29, 2017 (JP) .............................. JP2017-164673

(51) Int. Cl.
*A61B 6/00* (2006.01)
*G06K 9/00* (2022.01)
(Continued)

(52) U.S. Cl.
CPC ........... *G16H 50/30* (2018.01); *A61B 5/4064* (2013.01); *A61B 5/4848* (2013.01);
(Continued)

(58) Field of Classification Search
USPC ....... 382/100, 103, 128–134, 154, 162, 172, 382/173, 181, 199, 209, 219, 232, 254,
(Continued)

(56) References Cited

U.S. PATENT DOCUMENTS

2002/0095089 A1* 7/2002 Yamamoto ......... A61B 5/14553
128/897
2010/0010316 A1 1/2010 Fueyo et al.
(Continued)

FOREIGN PATENT DOCUMENTS

| JP | 2010017519 | 1/2010 |
| JP | 2011010828 | 1/2011 |

(Continued)

OTHER PUBLICATIONS

Bhavani S. Bagepally et al., "Relationship of Clinical and Cognitive Variables with Brain Morphometric Abnormalities in Alzheimer's Disease: a Voxel Based Morphometric Study Using 3-Tesla MRI", Oct. 2013, vol. 4, (Year: 2013).*

(Continued)

*Primary Examiner* — Seyed H Azarian
(74) *Attorney, Agent, or Firm* — JCIPRNET

(57) ABSTRACT

There are provided an information output apparatus, an information output method, and an information output program capable of outputting information effective for diagnosis or evaluation of dementia. In a case where a brain area having a high atrophy rate is input, the information output apparatus can output a test item highly relevant to the input brain area using a first table T1 that stores the relevance between a plurality of divided brain areas of a brain image and a plurality of test items of a dementia diagnostic test. In addition, in a case where a test item of interest is input, a brain area highly relevant to the input test item can be output.

6 Claims, 17 Drawing Sheets

(51) Int. Cl.
*G16H 50/30* (2018.01)
*G16H 10/60* (2018.01)
*G16H 30/40* (2018.01)
*A61B 5/00* (2006.01)
*G06T 7/00* (2017.01)

(52) U.S. Cl.
CPC ........... *G06T 7/0012* (2013.01); *G16H 10/60* (2018.01); *G16H 30/40* (2018.01); *G06T 2207/20021* (2013.01); *G06T 2207/30016* (2013.01)

(58) Field of Classification Search
USPC ...... 382/276, 286–291, 305, 321; 378/4, 21; 600/476
See application file for complete search history.

(56) References Cited

U.S. PATENT DOCUMENTS

| | | | |
|---|---|---|---|
| 2010/0179415 | A1 | 7/2010 | Wenzel et al. |
| 2011/0046451 | A1 | 2/2011 | Horn et al. |
| 2013/0251231 | A1* | 9/2013 | Goto .................... G06T 7/62 382/131 |
| 2016/0239968 | A1* | 8/2016 | Parsey ................ A61B 5/4088 |
| 2017/0024888 | A1* | 1/2017 | Ishii ..................... A61B 6/5217 |
| 2017/0042476 | A1* | 2/2017 | Reiman ................. A61B 6/032 |
| 2017/0273650 | A1 | 9/2017 | Ono et al. |
| 2018/0314691 | A1* | 11/2018 | Mori .................... A61B 5/055 |
| 2020/0107725 | A1* | 4/2020 | Tyler .................... A61B 8/485 |

FOREIGN PATENT DOCUMENTS

| | | |
|---|---|---|
| JP | 2014042684 | 3/2014 |
| JP | 2014145770 | 8/2014 |
| JP | 2016064004 | 4/2016 |

OTHER PUBLICATIONS

Bhavani S. Bagepally et al., "Relationship of Clinical and Cognitive Variables with Brain U I Morphometric Abnormalities in Alzheimer's Disease: a Voxel Based Morphometric Study Using 3-Tesla MRI", Oct. 2013, vol. 4, (Year: 2013).*

"International Search Report (Form PCT/ISA/210) of PCT/JP2018/021236," dated Jul. 3, 2018, with English translation thereof, pp. 1-5.

"Written Opinion of the International Searching Authority (Form PCT/ISA/237) of PCT/JP2018/021236," dated Jul. 3, 2018, with English translation thereof, pp. 1-7.

"Office Action of India Counterpart Application", dated Jun. 24, 2021, p. 1-p. 6.

S. D. Shenkin et al., "Cognitive Correlates of Cerebral White Matter Lesions and Water Diffusion Tensor Parameters in Community-Dwelling Older People", Cerebrovascular Diseases., Sep. 2, 2005, pp. 1-10.

Yang-Kun Chen et al., "Atrophy of the left dorsolateral prefrontal cortex is associated with poor performance in verbal fluency in elderly poststroke women", Neural Regeneration Research, Feb. 2013, pp. 1-12.

Flavio Nobili et al., "Resting SPECT—neuropsychology correlation in very mild Alzheimer's disease", Clinical Neurophysiology, Feb. 1, 2005, pp. 364-375.

Akira Niida et al., "Analysis of the presence or absence of atrophy of the subgenual and subcallosal cingulate cortices using voxel-based morphometry on MRI is useful to select prescriptions for patients with depressive symptoms", International Journal of General Medicine, Dec. 1, 2014, pp. 513-524.

"Search Report of Europe Counterpart Application", dated Oct. 30, 2020, p. 1-p. 10.

* cited by examiner

| NUMBER | DESCRIPTION OF NAME OF BRAIN AREA |
|---|---|
| 1, 2, 3 | POSTERIOR CENTRAL CONVOLUTION OR PRIMARY SOMATOSENSORY CORTEX |
| 4 | ANTERIOR CENTRAL CONVOLUTION OR PRIMARY MOTOR CORTEX |
| 5 | SOMATOSENSORY ASSOCIATION CORTEX |
| 6 | PREMOTOR CORTEX·SUPPLEMENTARY MOTOR AREA |
| 7 | SOMATOSENSORY ASSOCIATION CORTEX |
| 8 | FRONTAL EYE FIELD |
| 9 | DORSOLATERAL PREFRONTAL CORTEX |
| 10 | FRONTAL POLE |
| 11 | ORBITOFRONTAL CORTEX |
| 12 | ORBITOFRONTAL CORTEX |
| 13 | INSULAR CORTEX |
| 17 | PRIMARY VISUAL CORTEX (V1) |
| 18 | SECONDARY VISUAL CORTEX (V2) |
| 19 | ASSOCIATIVE VISUAL CORTEX (V3) |
| 20 | INFERIOR TEMPORAL GYRUS |
| 21 | MIDDLE TEMPORAL GYRUS |
| 22 | SUPERIOR TEMPORAL GYRUS |
| 23 | VENTRAL POSTERIOR CINGULATE CORTEX |
| 24 | VENTRAL ANTERIOR CINGULATE CORTEX |
| 25 | SUBGENUAL CORTEX |
| 26 | Ectosplenial area |
| 27 | PIRIFORM CORTEX |
| 28 | VENTRAL ENTORHINAL CORTEX |
| 29 | RETROSPLENIAL CORTEX |
| 30 | PART OF CINGULATE CORTEX |
| 31 | DORSAL POSTERIOR CINGULATE CORTEX |
| 32 | DORSAL ANTERIOR CINGULATE CORTEX |
| 33 | PART OF ANTERIOR CINGULATE CORTEX |
| 34 | DORSAL ENTORHINAL CORTEX (on the PARAHIPPOCAMPAL GYRUS) |
| 35 | PERIRHINAL CORTEX (on the PARAHIPPOCAMPAL GYRUS) |
| 36 | PARAHIPPOCAMPAL CORTEX (on the PARAHIPPOCAMPAL GYRUS) |
| 37 | FUSIFORM GYRUS |
| 38 | TEMPORAL POLE |
| 39 | ANGULAR GYRUS |
| 40 | SUPRAMARGINAL GYRUS |
| 41 | PRIMARY AUDITORY CORTEX |
| 42 | PRIMARY AUDITORY CORTEX |
| 43 | PRIMARY GUSTATORY CORTEX |
| 44 | INFERIOR FRONTAL GYRUS PARS OPERCULARIS |
| 45 | INFERIOR FRONTAL GYRUS PARS TRIANGULARIS |
| 46 | DORSOLATERAL PREFRONTAL CORTEX |
| 47 | PARS ORBITALIS |
| 48 | RETROSUBICULAR AREA |
| 52 | PARAINSULAR AREA |

FIG. 9

| | ITEM | POINT |
|---|---|---|
| 1 | WORD REPRODUCIBILITY | 4/10 |
| 2 | SPOKEN LANGUAGE | 3/5 |
| 3 | AUDITORY COMPREHENSION OF LANGUAGE | 2/5 |
| 4 | DIFFICULTY IN SPEAKING IN SPONTANEOUS SPEECH | 4/5 |
| 5 | ACCORDING TO VERBAL COMMAND | 3/5 |
| 6 | FINGER AND ARTICLE DESIGNATION | 2/5 |
| 7 | CONSTRUCTIVE ACTION (DRAWING) | 3/5 |
| 8 | IDEA MOVEMENT | 1/5 |
| 9 | ORIENTATION | 4/8 |
| 10 | WORD RECOGNITION | 8/12 |
| 11 | TEST TEACHING REPRODUCIBILITY | 2/5 |
| | TOTAL | 35/70 |

FIG. 10

| COORDINATE (x, y, z) | BRAIN AREA LABEL (NAME) |
|---|---|
| (0, 0, 0) | OUTSIDE BRAIN |
| ⋮ | ⋮ |
| (45, 50, 77) | DORSOLATERAL PREFRONTAL CORTEX (9) |
| ⋮ | ⋮ |
| (77, 91, 110) | ORBITOFRONTAL CORTEX (11) |
| ⋮ | ⋮ |

| BRAIN AREA NUMBER \ ELEVEN ITEM OF ADAS | 1 | 2 | ..... | 11 |
|---|---|---|---|---|
| 1 | RELEVANCE $A_{1,1}$ | | ..... | $A_{1,11}$ |
| ⋮ | ⋮ | ⋮ | ..... | ⋮ |
| 20 | RELEVANCE $A_{20,1} = 0.45$ | $A_{20,2}$ | ..... | $A_{20,11}$ |
| 21 | $A_{21,1}$ | $A_{21,2}$ | ..... | $A_{21,11}$ |
| 22 | RELEVANCE $A_{22,1} = 0.30$ | $A_{22,2}$ | ..... | $A_{22,11}$ |
| ⋮ | ⋮ | ⋮ | ..... | ⋮ |
| 52 | $A_{52,1}$ | $A_{52,2}$ | ..... | $A_{52,11}$ |

INFORMATION OUTPUT APPARATUS, INFORMATION OUTPUT METHOD, AND INFORMATION OUTPUT PROGRAM

CROSS-REFERENCE TO RELATED APPLICATIONS

This application is a Continuation of PCT International Application No. PCT/JP2018/021236 filed on Jun. 1, 2018, which claims priority under 35 U.S.C. § 119(a) to Japanese Patent Application No. 2017-164673 filed on Aug. 29, 2017. Each of the above application(s) is hereby expressly incorporated by reference, in its entirety, into the present application.

BACKGROUND OF THE INVENTION

1. Field of the Invention

The present invention relates to an information output apparatus, an information output method, and an information output program, and in particular, to a technique for providing (outputting) information effective for diagnosis of dementia and evaluation of a treatment method or a diagnostic method.

2. Description of the Related Art

With the arrival of an aging society, the number of patients with dementia is increasing year by year. Dementia develops in a case where a protein called amyloid β accumulates in the brain and accordingly brain atrophy progresses and cognitive ability declines. Since there is no cure for dementia, it is important in terms of maintaining the quality of life to detect brain atrophy early and start treatment early to delay the progression of dementia.

In order to meet such a demand, in recent years, information regarding the state of the brain can be acquired by nuclear medicine examinations such as single photon emission computed tomography (SPECT) and positron emission tomography (PET), CT images acquired by computerized tomography (CT) apparatuses, and MRI images acquired by magnetic resonance imaging (MRI) apparatuses. For example, decreased blood flow and metabolism in a local part of the brain can be found by checking a temporal change in the local part of the brain using SPECT and PET images.

On the other hand, brain atrophy can be found by calculating the volume of a specific part of the brain using MM images and comparing a temporal change in the volume.

JP2014-042684A discloses a medical image processing apparatus that divides the entire brain into a plurality of brain areas, calculates the degree of brain atrophy (amount of change) for each brain area, and displays a brain image in different colors according to the amount of change.

JP2011-010828A discloses a medical image display device that makes it possible to easily grasp on a three-dimensional composite image in which region of a diagnostic target part a lesion portion is present. In particular, the entire brain is divided into a plurality of brain areas, and it is displayed on a display unit in which brain area a lesion portion (cerebral infarction, brain tumor) is present. In addition, there is no description on brain atrophy or dementia in JP2011-010828A.

On the other hand, in the case of diagnosing dementia, a diagnostic test for dementia (for example, alzheimers' disease assessment scale (ADAS)) is performed as a neuropsychological test together with image diagnosis based on brain images, so that comprehensive diagnosis is performed.

SUMMARY OF THE INVENTION

The medical image processing apparatus described in JP2014-042684A calculates the degree of atrophy (amount of change) for each brain area and displays the brain image in different colors according to the amount of change. Therefore, the doctor can grasp changes in the brain tissue over time for each brain area, but there is a problem that it is difficult to correctly grasp the relevance between the neuropsychological diagnosis and the change in the brain form for each brain area.

On the other hand, the diagnostic test for dementia has a problem that the test result varies depending on the patient's mood, physical condition, educational history, and the like at the time of the diagnostic test.

The present invention has been made in view of such circumstances, and it is an object of the present invention to provide an information output apparatus, an information output method, and an information output program capable of outputting information effective for diagnosis or evaluation of dementia.

In order to achieve the aforementioned object, an information output apparatus according to an aspect of the present invention comprises: a first table that stores relevance between a plurality of divided brain areas of a brain image and a plurality of test items of a dementia diagnostic test; an input unit that inputs the brain areas; and an output unit that reads and outputs relevance of the plurality of test items corresponding to the brain areas or one or more test items, which have relevance exceeding a threshold value among the plurality of test items, from the first table based on the input brain areas and the first table.

The first table is a new table that can be created by collecting the analysis values of brain areas of brain images of a number of patients and the test results of diagnostic tests and processing the collected information. By processing more information, a highly reliable table can be obtained.

By using the first table, in a case where a brain area of interest (for example, a brain area having a high atrophy rate) is input, it is possible to acquire the relevance of a plurality of test items corresponding to the input brain area or highly relevant test items. That is, by inputting the brain area of interest, test items (cognitive function) that are highly relevant to the brain area can be seen.

An information output apparatus according to another aspect of the present invention comprises: a first table that stores relevance between a plurality of divided brain areas of a brain image and a plurality of test items of a dementia diagnostic test; an input unit that inputs the test items; and an output unit that reads and outputs relevance of the plurality of brain areas corresponding to the test items or one or more brain areas, which have relevance exceeding a threshold value among the plurality of brain areas, from the first table based on the input test items and the first table.

By using the first table, in a case where a test item of interest (for example, a test item for which the cognitive function has lowered) among the plurality of test items of the dementia diagnostic test is input, it is possible to acquire the relevance of a plurality of brain areas corresponding to the input test item or highly relevant brain areas. That is, by inputting the test item of interest, brain areas (for example, brain areas having a high atrophy rate) that are highly relevant to the test item can be seen.

An information output apparatus according to still another aspect of the present invention comprises: a first table that stores relevance between a plurality of divided brain areas of a brain image and a plurality of test items of a dementia diagnostic test; a second table that stores relevance between medicine information indicating a medicine used for treatment of dementia and one or more brain areas of the plurality of brain areas having significance for the medicine; an input unit that inputs medicine information indicating a medicine used for treatment of dementia; and an output unit that specifies a brain area having significance for the medicine based on the input medicine information and the second table and specifies and outputs one or more test items of the plurality of test items for the specified brain area based on the specified brain area and the first table.

The first table is a new table that can be created by collecting the analysis values of brain areas of brain images of a number of patients and the test results of diagnostic tests and processing the collected information. Similarly, the second table is a new table that can be created by using a medicine used for the treatment of dementia for a number of patients, analyzing images of a plurality of brain areas of brain images of the patients for whom the medicine has been used, collecting and processing the analysis values for the respective brain areas, and specifying one or more brain areas of the plurality of brain areas having significance for the medicine. The brain area having significance for the medicine is, for example, a brain area in which atrophy is suppressed compared with a case where no medicine is used.

By using the first table and the second table, in a case where medicine information indicating a specific medicine is input, a brain area having significance for the medicine indicated by the medicine information can be specified, and a test item highly relevant to the specified brain area among the plurality of test items of the dementia diagnostic test can be specified and output. That is, in a case where the medicine information indicating the medicine used for the treatment of dementia is input, one or more test items (test items to which focus is to be given) of the diagnostic test for which the effect of the medicine indicated by the medicine information can be expected can be acquired.

In addition, target patients for clinical trials for checking the effects or side effects of medicines can be easily determined using the test results of diagnostic tests that can be expected to be effective. Therefore, it is possible to reduce the burden on patients who do not require clinical trials obviously. In this manner, it is possible to improve the quality of clinical trials.

An information output apparatus according to still another aspect of the present invention comprises: a first table that stores relevance between a plurality of divided brain areas of a brain image and a plurality of test items of a dementia diagnostic test; a second table that stores relevance between medicine information indicating a medicine used for treatment of dementia and one or more brain areas of the plurality of brain areas having significance for the medicine; an input unit that inputs a test result of the diagnostic test for a patient; and an output unit that specifies one or more brain areas of the plurality of brain areas based on the input test result and the first table, specifies one or more medicines, which have significance for the specified brain areas and are used for treatment of dementia, based on the specified brain areas and the second table, and outputs medicine information indicating the specified medicines.

According to still another aspect of the present invention, in contrast to the information output apparatus described above, in a case where the test item of interest is input, a medicine used for the treatment of dementia can be specified using the first table and the second table and medicine information indicating the specified medicine can be output. That is, from the test result of the dementia diagnostic test for the subject (patient), the medicine information of one or more medicines suitable for the treatment of the patient can be acquired. Therefore, it is possible to support the selection of the medicine by the doctor.

In the information output apparatus according to still another aspect of the present invention, it is preferable that the plurality of brain areas are brain areas divided corresponding to a Broadmann's brain map.

An information output method according to still another aspect of the present invention comprises: a step of preparing a first table that stores relevance between a plurality of divided brain areas of a brain image and a plurality of test items of a dementia diagnostic test; a step of receiving an input of the brain areas; and a step of reading and outputting relevance of the plurality of test items corresponding to the brain areas or one or more test items, which have relevance exceeding a threshold value among the plurality of test items, from the first table based on the received brain areas and the first table.

An information output method according to still another aspect of the present invention comprises: a step of preparing a first table that stores relevance between a plurality of divided brain areas of a brain image and a plurality of test items of a dementia diagnostic test; a step of receiving an input of the test items; and a step of reading and outputting relevance of the plurality of brain areas corresponding to the test items or one or more brain areas, which have relevance exceeding a threshold value among the plurality of brain areas, from the first table based on the received test items and the first table.

An information output method according to still another aspect of the present invention comprises: a step of preparing a first table that stores relevance between a plurality of divided brain areas of a brain image and a plurality of test items of a dementia diagnostic test and a second table that stores relevance between medicine information indicating a medicine used for treatment of dementia and one or more brain areas of the plurality of brain areas having significance for the medicine; a step of receiving an input of medicine information indicating a medicine used for treatment of dementia; and a step of specifying a brain area having significance for the medicine based on the received medicine information and the second table and specifying and outputting one or more test items of the plurality of test items for the specified brain area based on the specified brain area and the first table.

An information output method according to still another aspect of the present invention comprises: a step of preparing a first table that stores relevance between a plurality of divided brain areas of a brain image and a plurality of test items of a dementia diagnostic test and a second table that stores relevance between medicine information indicating a medicine used for treatment of dementia and one or more brain areas of the plurality of brain areas having significance for the medicine; a step of receiving an input of a test result of the diagnostic test for a patient; and a step of specifying one or more brain areas of the plurality of brain areas based on the received test result and the first table, specifying one or more medicines, which have significance for the specified brain areas and are used for treatment of dementia, based on the specified brain areas and the second table, and outputting medicine information indicating the specified medicines.

The present invention according to still another aspect is an information output program applied to a computer comprising a first table that stores relevance between a plurality of divided brain areas of a brain image and a plurality of test items of a dementia diagnostic test. The program causes the computer to realize: a function of receiving an input of the brain areas; and a function of reading and outputting relevance of the plurality of test items corresponding to the brain areas or one or more test items, which have relevance exceeding a threshold value among the plurality of test items, from the first table based on the received brain areas and the first table.

The present invention according to still another aspect is an information output program applied to a computer comprising a first table that stores relevance between a plurality of divided brain areas of a brain image and a plurality of test items of a dementia diagnostic test. The program causes the computer to realize: a function of receiving an input of the test items; and a function of reading and outputting relevance of the plurality of brain areas corresponding to the test items or one or more brain areas, which have relevance exceeding a threshold value among the plurality of brain areas, from the first table based on the received test items and the first table.

The present invention according to still another aspect is an information output program applied to a computer comprising a first table that stores relevance between a plurality of divided brain areas of a brain image and a plurality of test items of a dementia diagnostic test and a second table that stores relevance between medicine information indicating a medicine used for treatment of dementia and one or more brain areas of the plurality of brain areas having significance for the medicine. The program causes the computer to realize: a function of receiving an input of medicine information indicating a medicine used for treatment of dementia; and a function of specifying a brain area having significance for the medicine based on the received medicine information and the second table and specifying and outputting one or more test items of the plurality of test items for the specified brain area based on the specified brain area and the first table.

The present invention according to still another aspect is an information output program applied to a computer comprising a first table that stores relevance between a plurality of divided brain areas of a brain image and a plurality of test items of a dementia diagnostic test and a second table that stores relevance between medicine information indicating a medicine used for treatment of dementia and one or more brain areas of the plurality of brain areas having significance for the medicine. The program causes the computer to realize: a function of receiving an input of a test result of the diagnostic test for a patient; and a function of specifying one or more brain areas of the plurality of brain areas based on the received test result and the first table, specifying one or more medicines, which have significance for the specified brain areas and are used for treatment of dementia, based on the specified brain areas and the second table, and outputting medicine information indicating the specified medicines.

According to the present invention, information effective for diagnosis or evaluation of dementia can be acquired by using the new first table that stores the relevance between a plurality of divided brain areas of the brain image and a plurality of test items of the dementia diagnostic test.

BRIEF DESCRIPTION OF THE DRAWINGS

FIG. 6 is a diagram showing a table T3 including numbers indicating brain areas and names of the respective brain areas.

FIG. 9 is a diagram showing diagnostic data indicating ADAS test results.

FIG. 10 is a diagram illustrating the association between three-dimensional information of all voxels forming a brain image and brain area labels.

DESCRIPTION OF THE PREFERRED EMBODIMENTS

Hereinafter, preferred embodiments of an information output apparatus, an information output method, and an information output program according to the present invention will be described with reference to the accompanying diagrams.

<Apparatus Configuration>

Figure 1:
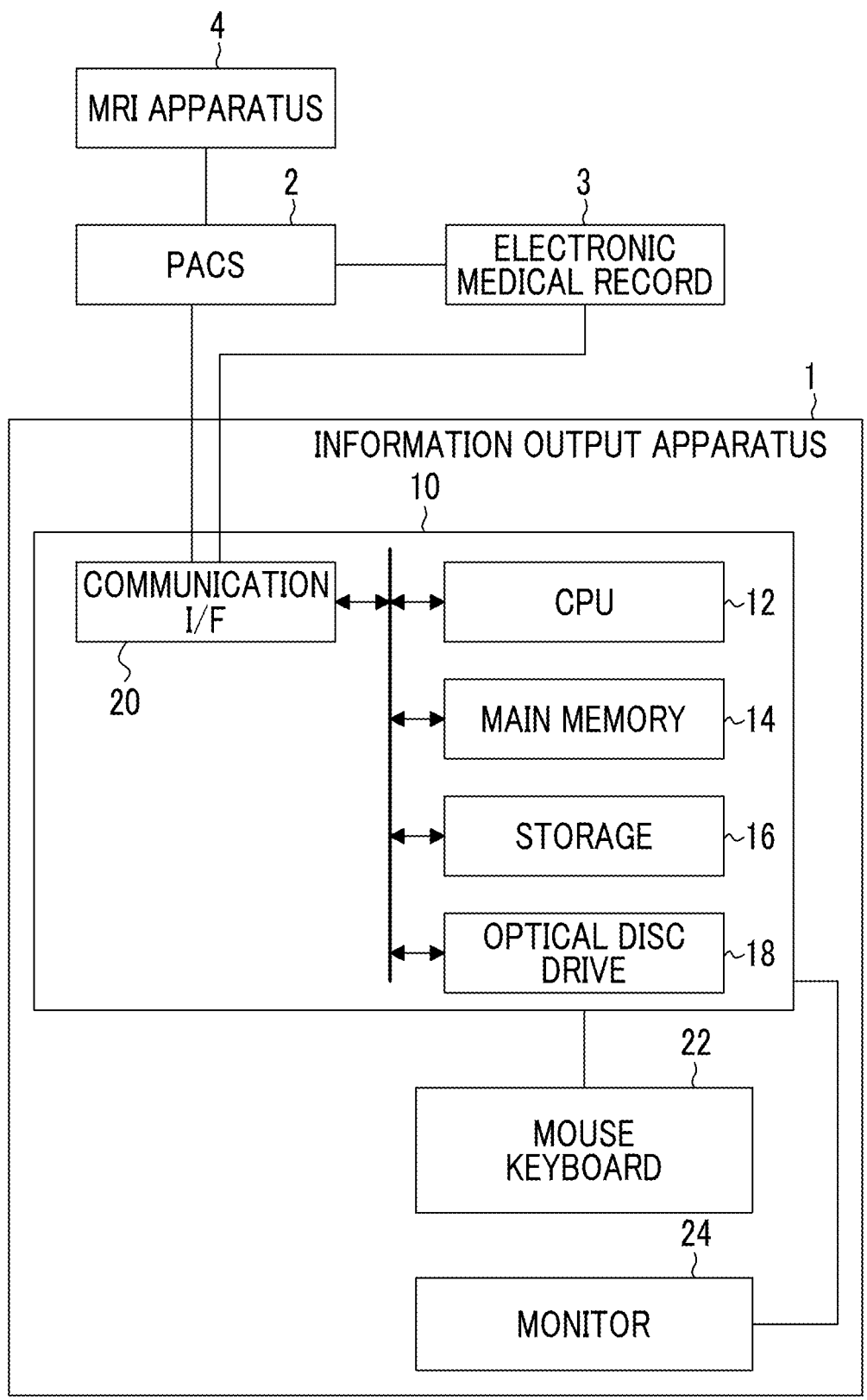
FIG. 1 is a hardware configuration diagram showing the outline of a system including an information output apparatus according to the present invention.

FIG. 1 is a hardware configuration diagram showing the outline of a system including an information output apparatus according to the present invention.

The system shown in FIG. 1 is configured to include an information output apparatus 1, picture archiving and communication systems (PACS) 2, an electronic medical record 3, and a magnetic resonance imaging (MM) apparatus 4.

The MRI apparatus 4 continuously measures nuclear magnetic resonance signals from hydrogen, phosphorus, and the like in a subject and visualizes the nuclear density distribution, relaxation time distribution, and the like, and is an apparatus that acquires a three-dimensional image showing a part as a diagnostic target of a patient who is the subject. As an apparatus for acquiring a three-dimensional image of a subject, there is a CT apparatus capable of acquiring a computed tomography (CT) image in addition to the MM apparatus 4.

In the present invention, a diagnostic target part of a patient who is a subject is a brain, and the MRI apparatus 4 outputs an MRI image of the head including the brain of the subject as a three-dimensional brain image.

The three-dimensional brain image is configured as a set of axial tomographic images (slice images) according to a predetermined slice interval or slice thickness (for example, a group of several hundred images). A voxel in each slice image corresponds to a pixel of a two-dimensional image having a slice thickness, and each voxel has three-dimensional information.

The PACS 2 is a unit that centrally manages digital medical image information, which is obtained from a plurality of examination apparatuses (modalities), as electronic data. A three-dimensional brain image captured by the MM apparatus 4 that is one of the modalities is stored and managed by the PACS 2 and used for searching, browsing, and the like by the electronic medical record 3 or the information output apparatus 1.

In the PACS 2, image storage and communication are performed using the image format and communication protocol of digital imaging and communication in medicine (DICOM). In the image format of the DICOM standard, parameters, diagnostic information, and the like at the time of imaging can be stored in the header portion of the file. In the present embodiment, it is assumed that a plurality of three-dimensional brain images having different imaging dates and times for the same subject are stored and managed in the PACS 2.

The information output apparatus 1 is obtained by installing an information output program according to the present invention on one computer 10, and the computer may be a workstation or a personal computer that is directly operated by the doctor who performs diagnosis or may be a server computer connected to these through a network.

The information output program is distributed in a state in which the information output program is recorded on an optical disc (recording medium), such as a digital versatile disc (DVD) or a compact disk read only memory (CD-ROM), and is installed from the optical disc onto the computer 10 through an optical disc drive 18.

An operation unit 22, such as a mouse and a keyboard that function as an input unit, and a monitor 24 are connected to the computer 10.

The computer 10 is configured to mainly include: a central processing unit (CPU) 12 that perform overall control of the operation of each component; a main memory 14 that stores an apparatus control program or serves as a working area at the time of executing the program; a storage 16, such as a hard disk drive; the optical disc drive 18 for reading and writing various kinds of data and programs recorded on the optical disc; and a communication interface (communication I/F) 20 for exchanging necessary information with the PACS 2, the electronic medical record 3, and the like.

In addition to various kinds of application software including an information output program according to the present invention, a reference brain image, and various tables (will be described later) used in the present invention, brain images of the subject acquired from the PACS 2 through the communication I/F 20 and various kinds of information including diagnostic information acquired from the electronic medical record 3 are stored in the storage 16. The diagnostic information includes data indicating the test results of alzheimers' disease assessment scale (ADAS) or ADAS-Jcog (alzheimer's disease assessment scale Japanese version).

Figure 2:
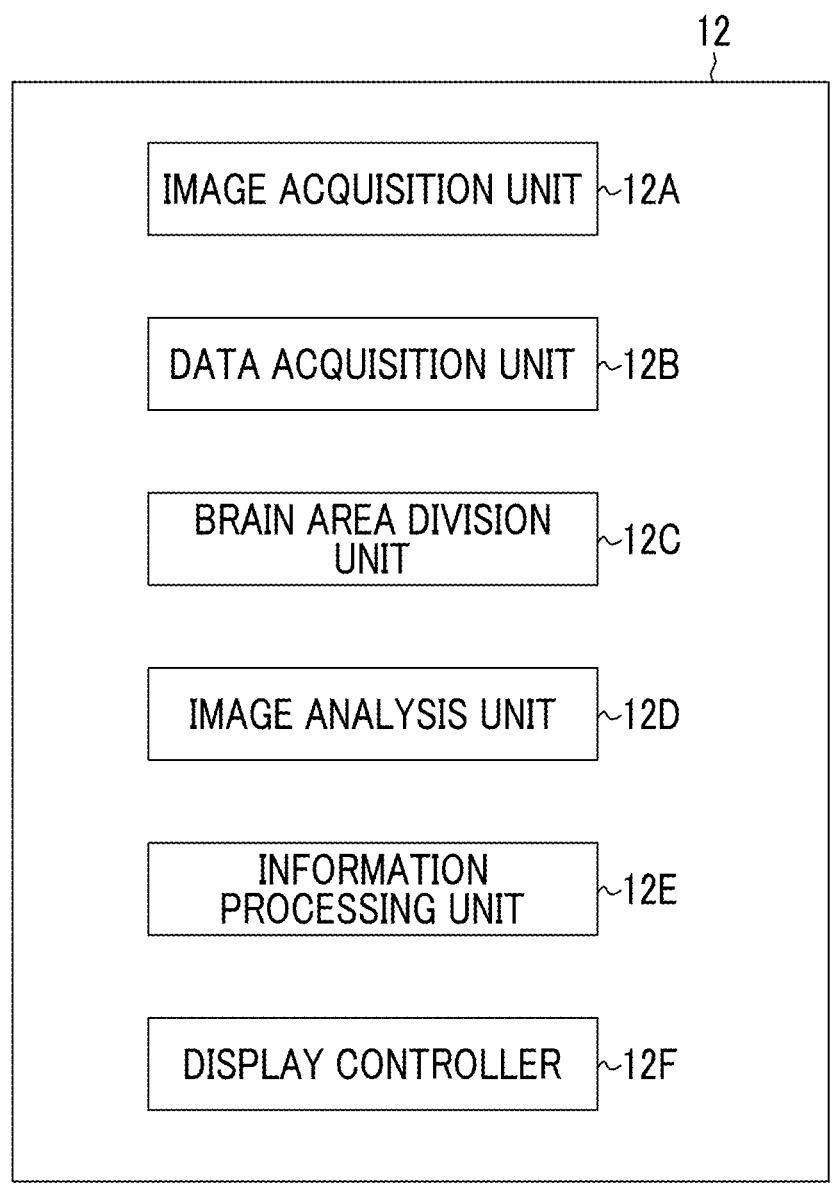
FIG. 2 is a functional block diagram showing a function of a CPU of the information output apparatus shown in FIG. 1.

FIG. 2 is a functional block diagram showing a function of a CPU 12 of the information output apparatus 1 shown in FIG. 1.

The CPU 12 functions as various processing units by executing the information output program stored in the storage 16. In this embodiment, the CPU 12 has functions as an image acquisition unit 12A, a data acquisition unit 12B, a brain area division unit 12C, an image analysis unit 12D, an information processing unit 12E, and a display controller 12F.

The image acquisition unit 12A acquires a three-dimensional standard brain image Bs and a three-dimensional first brain image B1 and a three-dimensional second brain image B2 including the brain of the same subject and having different imaging dates and times.

The standard brain image Bs is a three-dimensional brain image showing a brain having a standard shape and size and a standard density (pixel value), that is, a standard brain. The standard brain image Bs can be generated by extracting brains from a plurality of brain images, which are acquired by imaging the heads of a plurality of healthy persons with a three-dimensional image capturing apparatus, and averaging the plurality of extracted brains.

The standard brain image Bs includes division information for dividing the entire brain into a plurality of brain areas. As a method of division, for example, based on the Broadmann's brain map, within the three-dimensional region of the cerebral cortex, it is possible to use a method of dividing the cerebral cortex into brain areas responsible for functions, such as movement, language, perception, memory, vision sense, and acoustic sense. In addition, it is possible to use any known method, such as a method for division into six kinds of brain areas of cerebrum, diencephalon, mesencephalon, hindbrain, cerebellum, and medulla oblongata and a method of dividing the cerebrum into frontal lobe, parietal lobe, temporal lobe, and occipital lobe.

Figure 3:
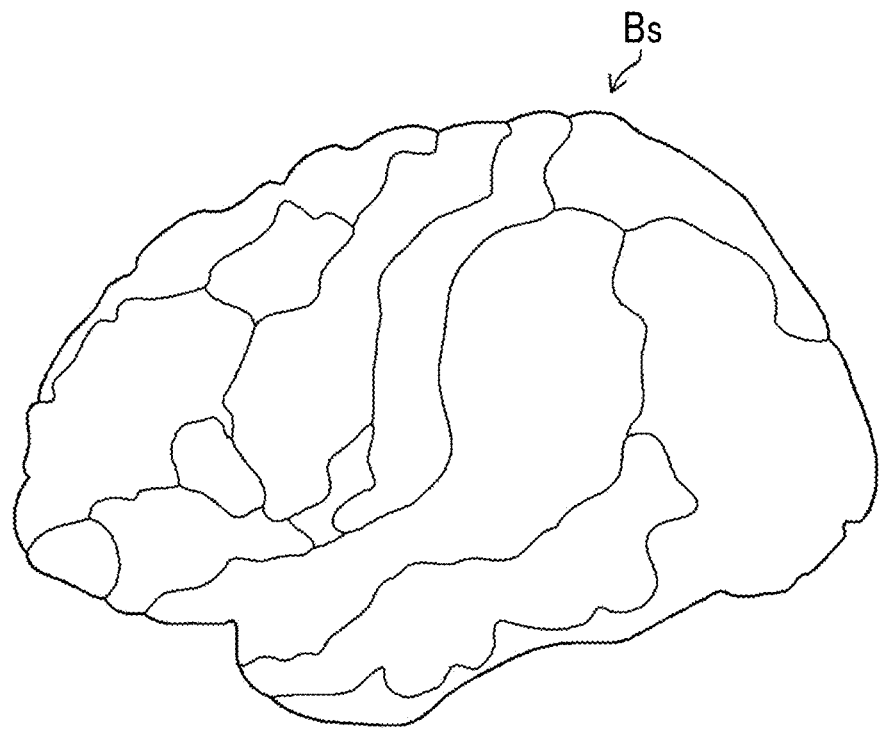
FIG. 3 is a diagram showing a standard brain image including division information.

FIG. 3 is a diagram showing an example of the standard brain image Bs including division information, and the entire brain is divided into a plurality of brain areas. In this example, the standard brain image Bs is divided into a plurality of brain areas. For example, the standard brain image Bs is divided into a plurality of brain areas according to the Broadmann's brain map. In the brain area, a ventricle and a cavity other than the ventricle (a cavity filled with cerebrospinal fluid) may be the brain area.

The image acquisition unit 12A can acquire the standard brain image Bs from the storage 16 or the PACS 2. In addition, the image acquisition unit 12A can acquire a first brain image B1 (FIG. 4) and a second brain image B2 (not shown) of the same subject having different imaging dates and times from the PACS 2 or the electronic medical record 3. In this example, the first brain image B1 has an imaging date and time earlier than that of the second brain image B2, for example, an image six months or one year ago.

The data acquisition unit 12B acquires a table T3 shown in FIG. 6, diagnostic information (in this example, diagnostic data indicating a test result in ADAS) D1 shown in FIG. 9, and the like. The table T3 and the diagnostic data D1 are used for display control of medical images and medical information in a case where the information output apparatus 1 functions as a viewer.

In the table T3 shown in FIG. 6, numbers indicating brain areas (Broadmann field: 1 to 52) and descriptions of name and function of each brain area are stored so as to be associated with each other. Known data can be used as the data of the table T3. The table T3 can be stored in the storage 16 in advance, and can be read and used appropriately.

Figure 7:
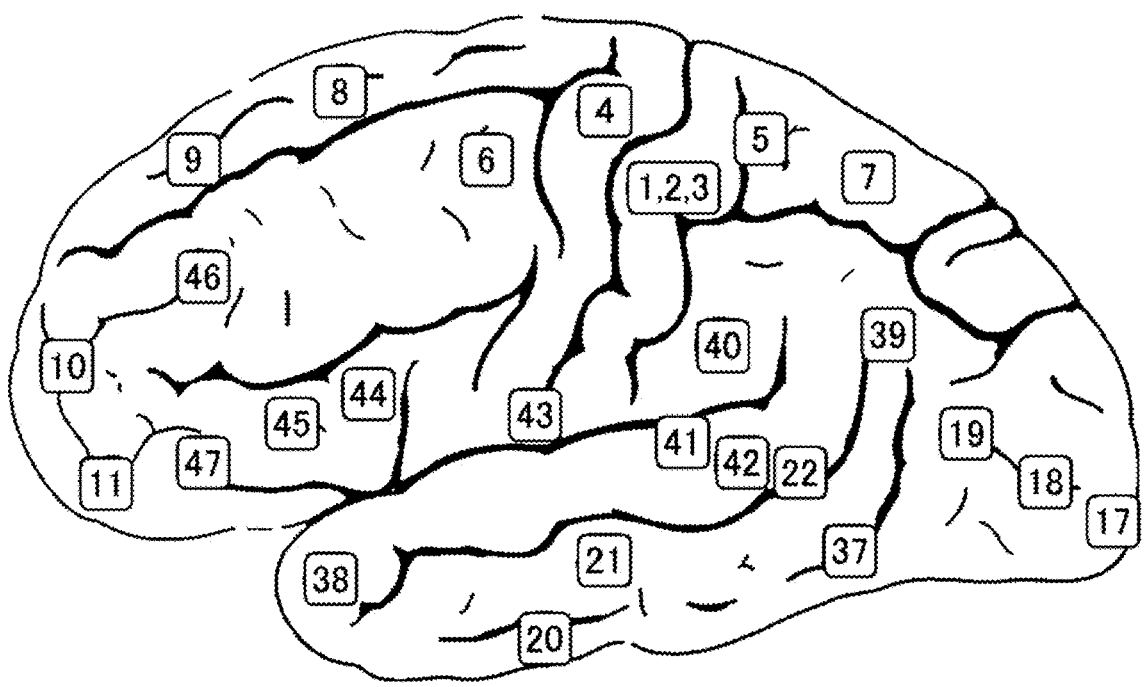
FIG. 7 is a diagram in which a brain image on the outer surface is numbered to indicate brain areas.
Figure 8:
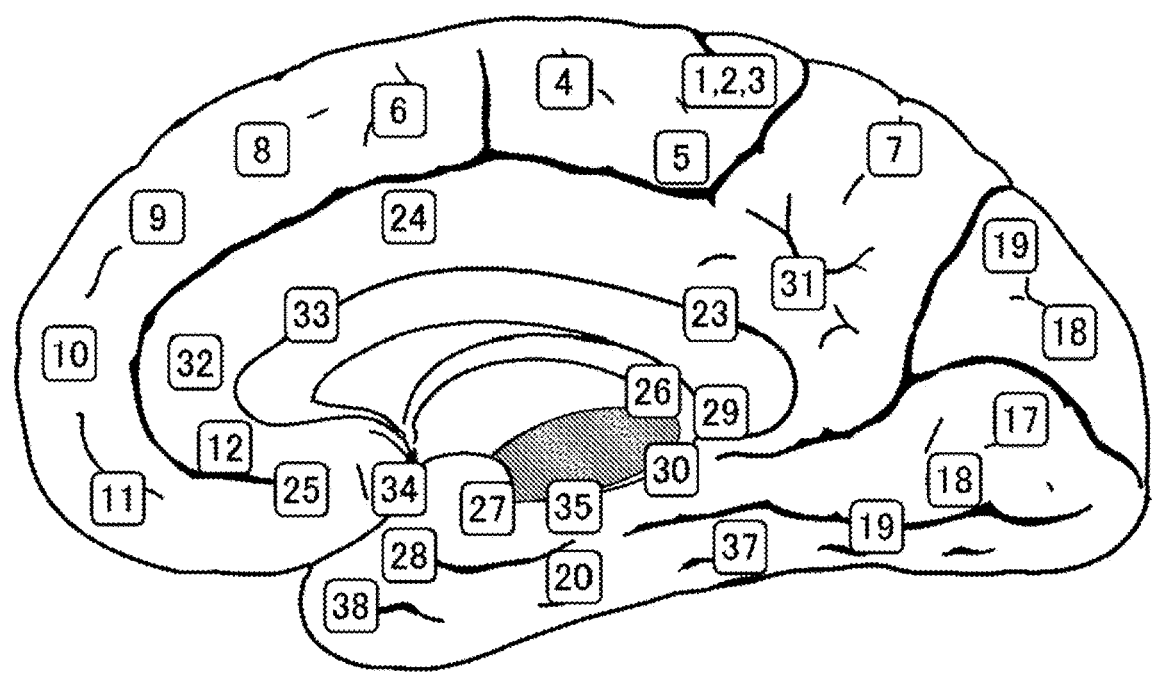
FIG. 8 is a diagram in which a brain image on the inner surface is numbered to indicate brain areas.

FIG. 7 is a diagram in which a brain image on the outer surface is numbered to indicate brain areas, and FIG. 8 is a diagram in which a brain image on the inner surface is numbered to indicate brain areas.

The ADAS is one of various cognitive function evaluations. The ADAS is for evaluating the cognitive function centered on memory in order to test dementia. As shown in FIG. 9, evaluation is performed based on eleven test items of word reproducibility, spoken language ability, auditory comprehension of language, difficulty in speaking in spontaneous speech, according to verbal command, finger and article designation, constructive action, idea movement, orientation, word recognition, and test teaching reproducibility and the ADAS score of 0 to 70 points. The score is obtained by subtracting the number of correct answers from the full score of each test item. In a case where all questions are correct, the score is 0. In the example shown in FIG. 9, there is error in 35 questions. For example, the test item 4 "difficulty in speaking in spontaneous speech" is wrong in 4 of 5 questions.

The data acquisition unit 12B can acquire diagnostic data D1 (FIG. 9) indicating the ADAS test result from, for example, the electronic medical record 3 or the header portion of the image file complying with the DICOM standard. The cognitive function evaluation is not limited to ADAS and ADAS-Jcog, and mini mental state examination (MMSE), Wechsler adult intelligence scale-III (WAIS-III), revised Hasegawa type simple intelligence evaluation scale, and the like can be used.

Returning to FIG. 2, the brain area division unit 12C is a unit that divides each of the three-dimensional first brain image B1 and the three-dimensional second brain image B2 into a plurality of brain areas.

Figure 4:
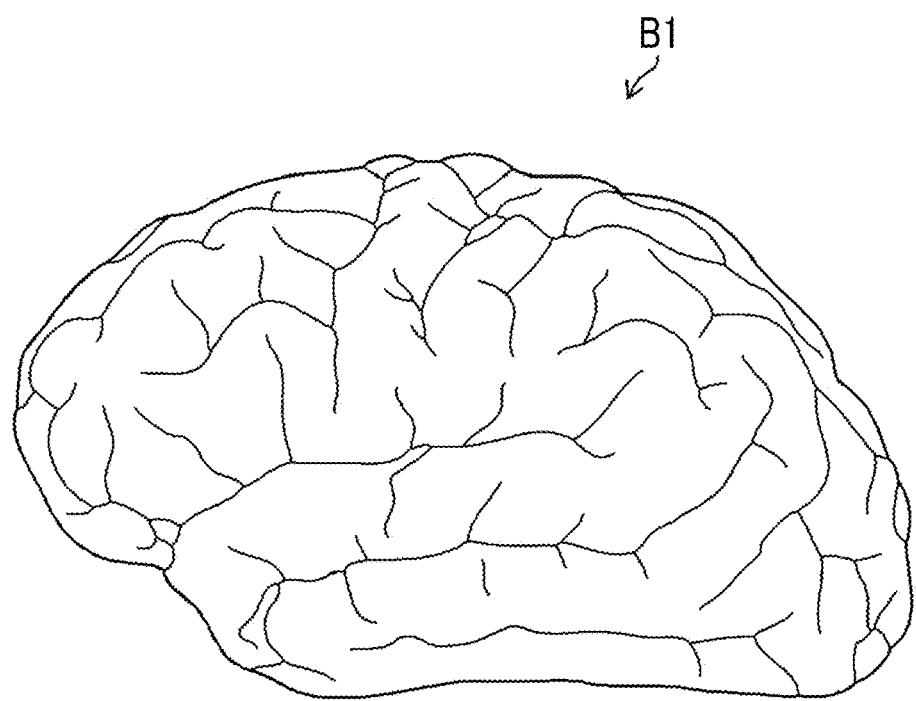
FIG. 4 is a diagram showing a first brain image.

First, the brain area division unit 12C performs registration between the standard brain image Bs shown in FIG. 3 and the first brain image B1 shown in FIG. 4. The size and shape of the brain vary from person to person. For example, in a case where the brain is compared with the standard brain, the size and shape of the brain are different by about ±15% at the maximum.

The standard brain image Bs and the first brain image B1 have different sizes and shapes. Therefore, in order to divide the first brain image B1 into a plurality of brain areas, the brain area division unit 12C performs first registration using landmarks common to the standard brain image Bs and the first brain image B1.

As landmarks, specifically, feature points of characteristic regions, such as a number of cerebral sulci (upper frontal sulcus, inferior frontal sulcus, lateral sulcus, longitudinal cerebral fissure, and the like) and ventricles (left and right lateral ventricles of the cerebral hemisphere, third ventricle, and fourth ventricle) included in the brain, can be used. In this example, it is assumed that the standard brain image Bs is registrated with the first brain image B1. This is because causing no deformation of the first brain image B1 can improve the calculation accuracy of the analysis value (such as the atrophy rate of the brain area) by the image analysis unit 12D to be described later.

The brain area division unit 12C extracts landmarks from the standard brain image Bs and the first brain image B1 for registration. For example, landmarks may be extracted by template matching using a template indicating a landmark, or may be extracted using a discriminator that has been learned to discriminate landmarks included in an image.

The brain area division unit 12C performs first registration so that corresponding landmarks (feature points) match each other between the standard brain image Bs and the first brain image B1. In the present embodiment, the first registration is registration by similarity transformation. Specifically, the first registration is registration by parallel movement, rotation, and similar enlargement and reduction of the standard brain image Bs. The brain area division unit 12C performs the first registration by performing similarity transformation of the standard brain image Bs so that the correlation between the landmark included in the standard brain image Bs and the corresponding landmark included in the first brain image B1 is maximized.

After performing the first registration, the brain area division unit 12C performs second registration for matching the standard brain image Bs with the first brain image B1 using the corresponding landmarks. The second registration is registration by nonlinear transformation. As the registration by nonlinear transformation, for example, there is registration performed by nonlinearly transforming pixel positions using functions, such as B spline and thin plate spline.

The brain area division unit 12C performs the second registration by nonlinearly transforming each pixel position of the standard brain image Bs after the first registration into a corresponding pixel position included in the first brain image B1.

Figure 5:
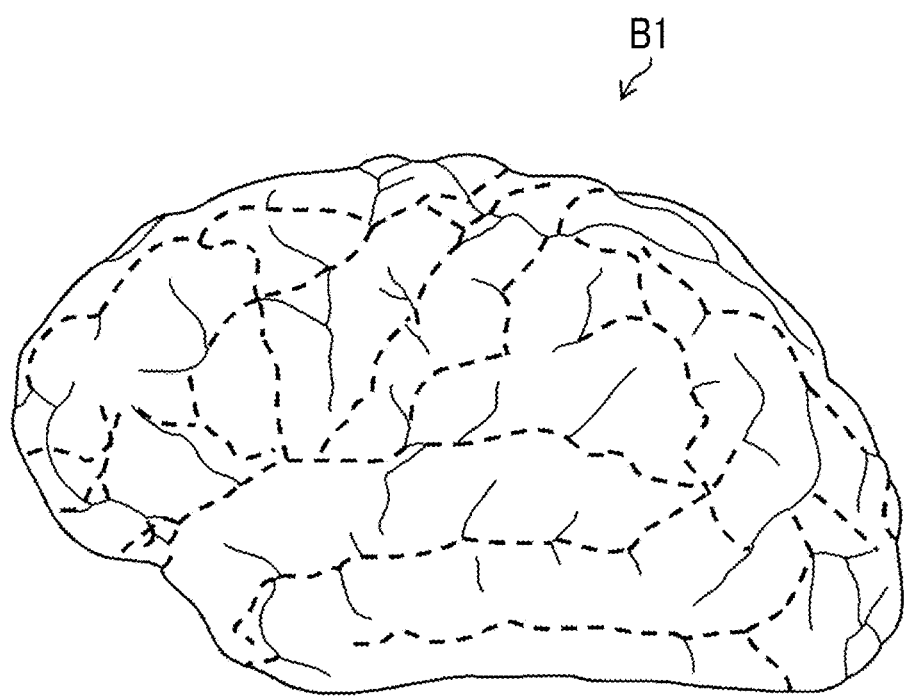
FIG. 5 is a diagram showing a first brain image divided into a plurality of brain areas.

By applying three-dimensional information (division information after registration) of the boundary between brain areas divided in the standard brain image Bs to the first brain image B1 after registrating the standard brain image Bs with the first brain image B1 as described above, the brain area division unit 12C can divide the first brain image B1 into a plurality of brain areas as shown by the broken lines in FIG. 5.

The brain area division unit 12C divides the second brain image B2 into brain areas. Specifically, third registration is performed using landmarks between the first brain image B1 and the second brain image B2. In the third registration, image enlargement and reduction are not performed, and parallel movement and rotation of the first brain image B1 are performed to registrate the first brain image B1 with the second brain image B2. Alternatively, the second brain image B2 may be registrated with the first brain image B1.

Since the first brain image B1 and the second brain image B2 are brain images of the same subject having different imaging dates and times, both the brain images after the third registration have a very high degree of matching. That is, the three-dimensional position of a certain pixel (voxel) in the three-dimensional first brain image B1 and a voxel of the second brain image B2 corresponding to the voxel are present at the same three-dimensional position or the vicinity thereof.

Therefore, the brain area division unit 12C can match each voxel of the first brain image B1 and each voxel of the second brain image B2 with each other by corresponding point matching based on local image features centered on the corresponding voxels, for example.

The brain area division unit 12C can divide the second brain image B2 into a plurality of brain areas by performing matching between all voxels of each voxel of the first brain image B1 and each voxel of the second brain image B2. That is, three-dimensional information of each voxel of the second brain image B2 acquired by acquiring three-dimensional information of each voxel of the second brain image B2 corresponding to each voxel (that is, a voxel based on the division information) of the boundary of the plurality of brain areas of the first brain image B1 is division information for dividing the second brain image B2 into a plurality of brain areas.

The method of dividing the first brain image B1 and the second brain image B2 into a plurality of brain areas by the brain area division unit 12C is not limited to the embodiment described above, and various known methods can be applied. For example, a method described in JP2011-010828A can be applied.

The brain area division unit 12C divides the first brain image B1 into a plurality of brain areas so that three-dimensional information (coordinates x, y, z) and brain area labels (numbers indicating brain areas) and/or names are associated with each other for all voxels forming the three-dimensional first brain image B1 as shown in FIG. 10, and temporarily stores the results in the main memory 14 or stores the results in the storage 16. Similarly, also for the second brain image B2, three-dimensional information and brain area labels and the like are associated with each other for all voxels, and the results are stored in the main memory 14 or the storage 16. In addition, it is preferable to store the correspondence between each voxel of the first brain image B1 and each voxel of the second brain image B2. This is because a voxel movement vector can be calculated based on the three-dimensional information between corresponding voxels.

Each coordinate axis of the three-dimensional information (coordinates x, y, z) of the brain image corresponds to each body axis (X axis: left-right, Y axis: back-abdomen, Z axis: head-tail). The origin (0, 0, 0) can be set at a specific position outside or inside the brain, for example.

The image analysis unit 12D is a unit that analyzes the first brain image B1 and the second brain image B2 for each divided brain area and outputs the analysis result (analysis value). For example, analysis results, such as an atrophy rate, a volume change amount, a shape change amount, a Z score, and a blood flow volume for each brain area, are output.

Figure 11:
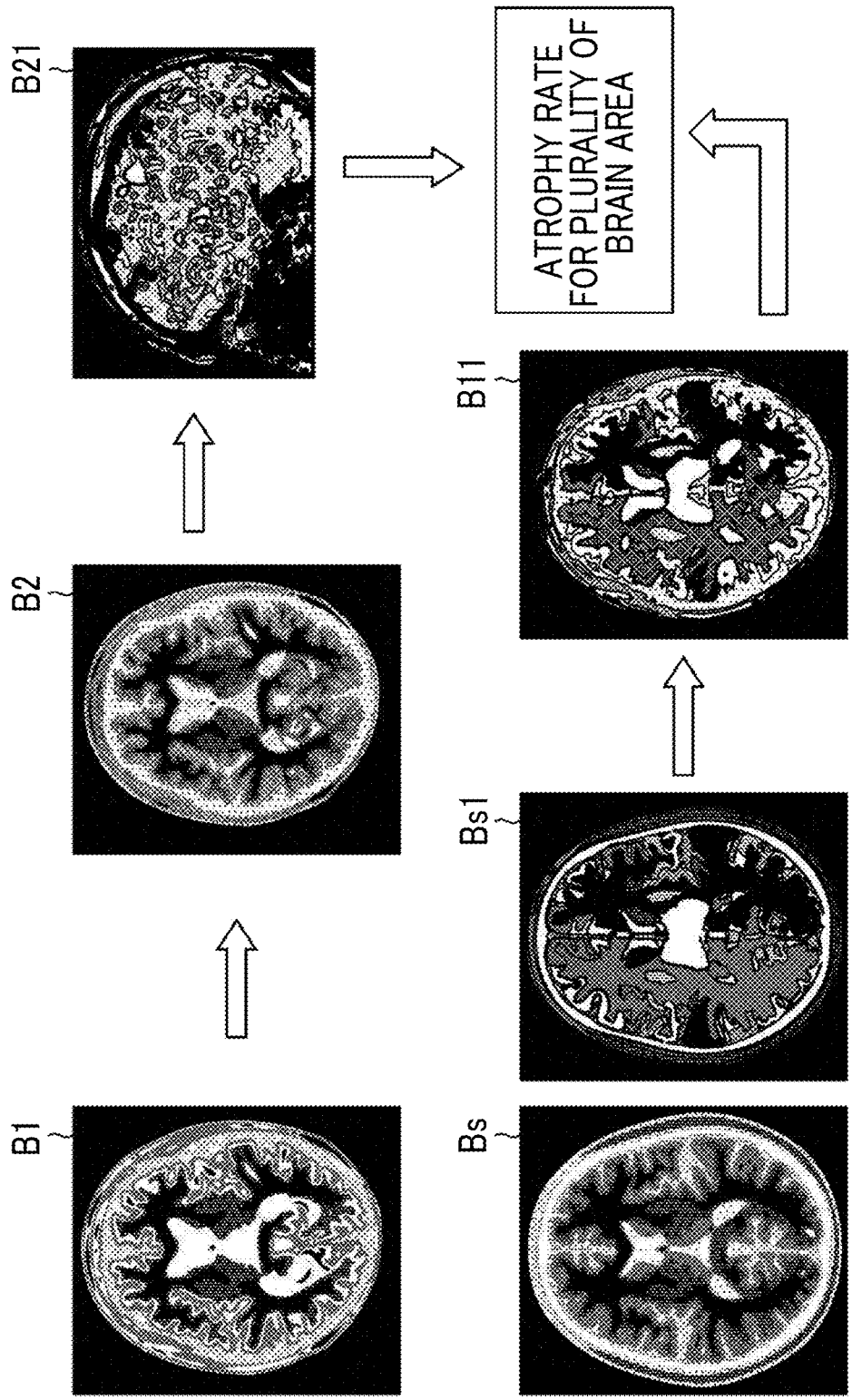
FIG. 11 is a diagram showing the flow of a process of a brain area division unit and a process of an image analysis unit.

FIG. 11 is a diagram showing the flow of processing of the brain area division unit 12C and processing of the image analysis unit 12D.

In FIG. 11, the standard brain image Bs includes division information for dividing the entire brain into a plurality of brain areas. Bs1 indicates a plurality of brain areas (division information) of the standard brain image Bs. By registering the standard brain image Bs with the first brain image B1, division information indicating the plurality of brain areas of the standard brain image Bs after the registration can be used as division information (B11) indicating the plurality of brain areas of the first brain image B1.

By applying the first brain image B1 having the division information of the plurality of brain areas to the second brain image B2 and performing association between the voxels, the second brain image B2 can be substantially divided into the plurality of brain areas. B21 is a diagram showing a plurality of brain areas of the second brain image B2. B11 indicates a plurality of brain areas of the first brain image B1 in the axial section, and B21 indicates a plurality of brain areas of the second brain image B2 in the sagittal section.

The image analysis unit 12D calculates the volumes of the plurality of brain areas of the first brain image B1 and the plurality of brain areas of the second brain image B2 for each same brain area. After calculating the volume, the atrophy rate of the brain is calculated as an analysis value for each brain area by subtracting the volume of the corresponding brain area of the first brain image B1 from the volume of the brain area of the second brain image B2 and dividing a value obtained as a result of the subtraction by the volume of the corresponding brain area of the first brain image B1.

The brain area atrophies in a case where the atrophy rate is a positive value, and expands in a case where the atrophy rate is a negative value. The volume of the brain area can be calculated by counting the number of voxels in the brain area (the volume per voxel is known).

In this example, the image analysis unit 12D calculates the atrophy rate as an analysis value for each of the plurality of brain areas. However, the volume change amount, the shape change amount, the Z score, and the blood flow volume for each brain area may be calculated as analysis values.

The volume change amount for each brain area can be calculated by subtracting the volume of the corresponding brain area of the first brain image B1 from the volume of the brain area of the second brain image B2.

The shape change amount can be calculated from the change amount of the sphericity of the corresponding brain areas of the first brain image B1 and the second brain image B2, for example. The sphericity can be determined by the ratio of the surface area of a sphere having the same volume as the brain area to the surface area of the brain area. In addition, the sphericity can be determined by calculating the absolute value of a change region between the brain area of the first brain image B1 and the corresponding brain area of the second brain image B2.

The Z score can be calculated for each brain area of the first brain image B1 and the second brain image B2 based on the following equation.

$$Z = (x_{ave} - x)/\sigma \qquad \text{[Equation 1]}$$

Here, x: voxel value, $x_{ave}$: average value of voxel values of healthy persons, $\sigma$: standard deviation of voxel values of healthy persons.

The image analysis unit 12D can calculate the blood flow volume for the first brain image B1 and the second brain image B2 by an arterial spin labeling (ASL) brain perfusion examination for evaluating the blood flow dynamics of the brain without using a contrast medium.

Figure 12:
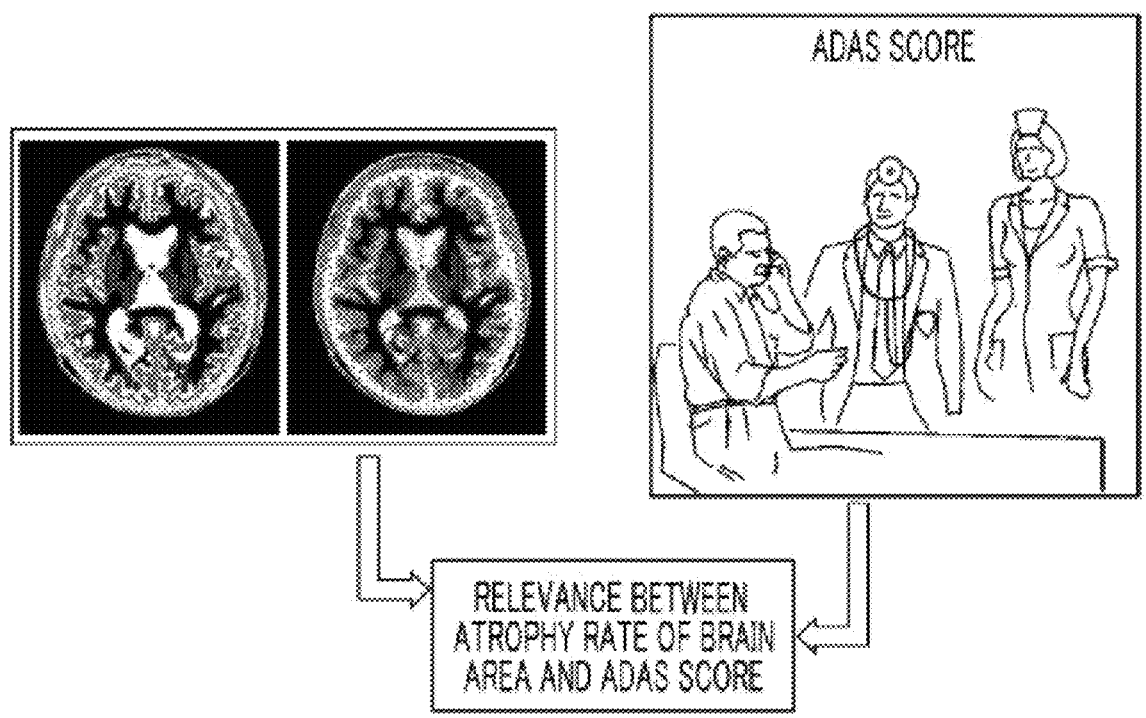
FIG. 12 is a diagram used to describe the creation of a first table.

The information processing unit 12E is a unit that calculates the relevance between a plurality of divided brain areas of the brain image and a plurality of test items of the diagnostic test for dementia and creates a table (first table T1 (FIG. 16)) that stores the relevance between a plurality of brain areas (in this example, brain areas of 1 to 52) and a plurality of test items (in this example, test items of 1 to 11). As shown in FIG. 12, an analysis value for each brain area of the brain image of the patient (in this example, an atrophy rate of each brain area) and the test result of the diagnostic test for dementia (in this example, the ADAS score) are collected, and the relevance between the atrophy rate and the test items is calculated.

Specifically, in creating the first table T1, the information processing unit 12E acquires the atrophy rate of each brain area of brain images of a number of patients and the score for each of the eleven test items of the ADAS from the image analysis unit 12D and the data acquisition unit 12B.

Figure 13:
FIG. 13 is a correlation diagram showing correlation between the score and the atrophy rate of a test item.
Figure 14:
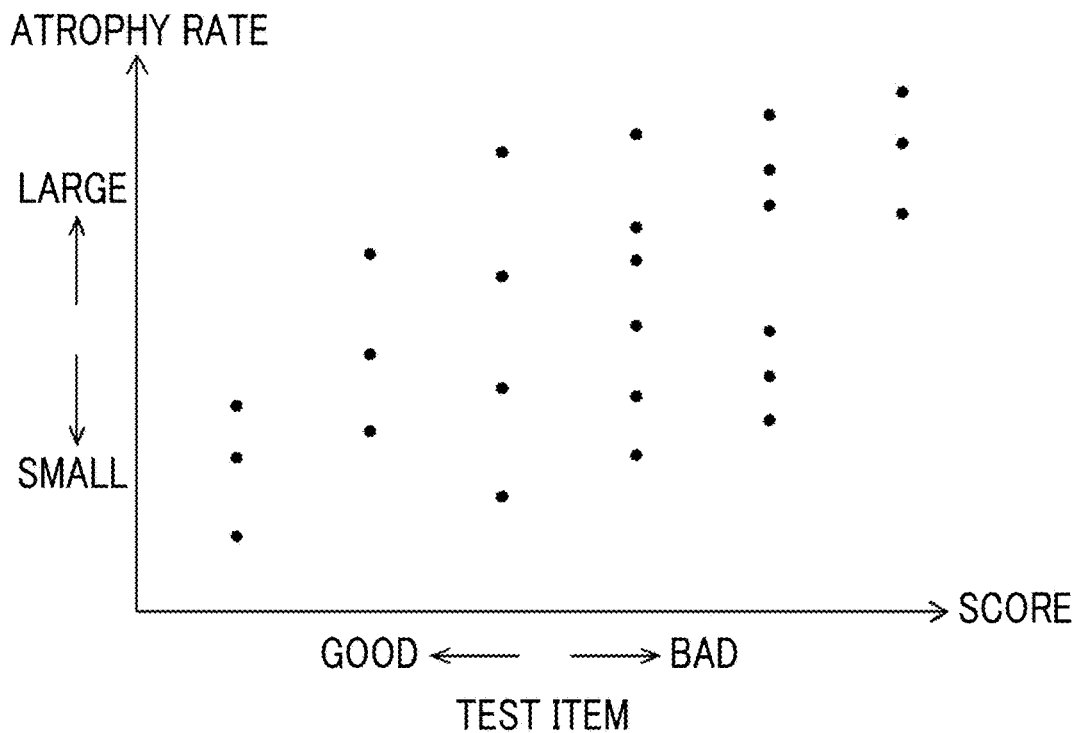
FIG. 14 is another correlation diagram showing correlation between the score and the atrophy rate of a test item.
Figure 15:
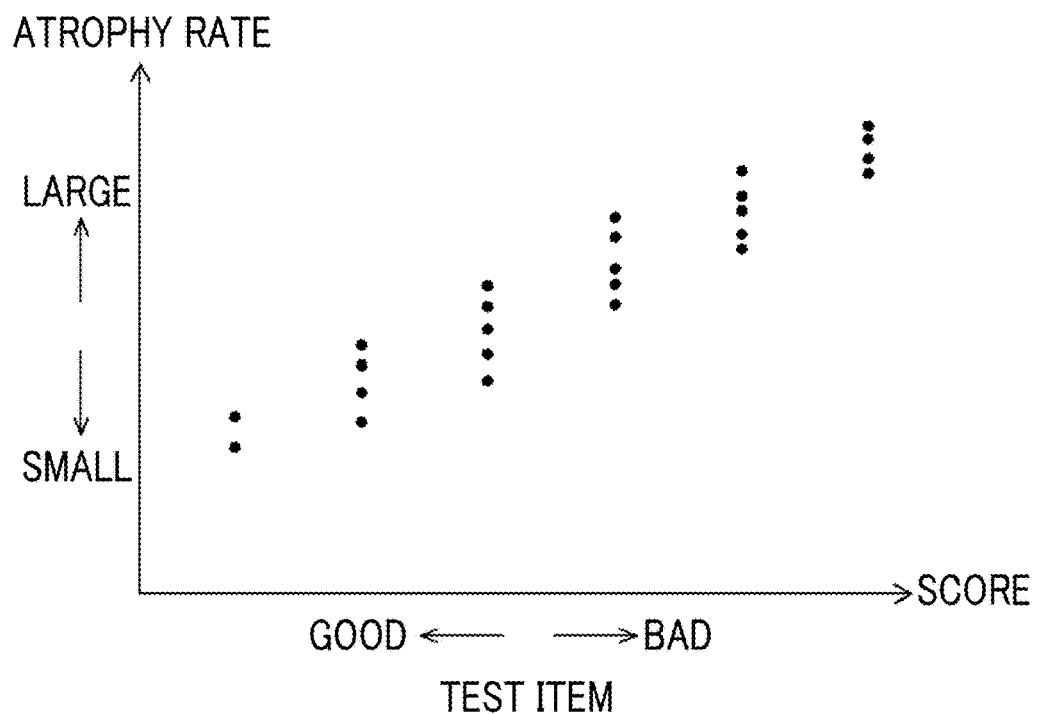
FIG. 15 is still another correlation diagram showing correlation between the score and the atrophy rate of a test item.

FIGS. 13 to 15 are correlation diagrams showing the correlation between the score of each test item and the atrophy rate.

The horizontal axis in the correlation diagrams shown in FIGS. 13 to 15 indicates one test item of the eleven test items of ADAS, and the vertical axis in the correlation diagrams indicates the atrophy rate of one brain area of a plurality of brain areas. In the ADAS, the number of correct answers is subtracted from the full score of the test item to obtain a score. Therefore, the higher the score, the more incorrect answers and the worse the evaluation of the cognitive function.

FIG. 13 shows a case where there is almost no correlation between the score of the test item and the atrophy rate, FIG. 14 shows a positive weak correlation, and FIG. 15 shows a positive strong correlation.

Figure 16:
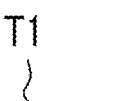
FIG. 16 is a diagram schematically showing a first table.

The information processing unit 12E calculates the relevance between the atrophy rate of each brain area of the brain image and the score for each test item, and creates the first table T1 indicating the relevance as shown in FIG. 16.

In FIG. 16, $A_{ij}$ ($1 \le i \le 52$, $1 \le j \le 11$) indicates the relevance, and can be a correlation value of $-1 \le A_{ij} \le 1$. In the brain area, atrophy progresses over time. However, for example, in a case where the ventricle and other cavities are divided as brain areas, the brain area expands. Therefore, in this case, a negative correlation value is obtained. In addition, FIG. 16 shows the relevance ($A_{20,1}$=0.45, $A_{21,1}$=0.30) between the test item (item 1) of ADAS and the brain areas (lower temporal gyms, upper temporal gyms) indicated by numbers 20 and 22. However, these relevance values are not actually calculated values.

The first table T1 created by the information processing unit 12E is stored in, for example, the storage 16, and is appropriately used as necessary by the display controller 12F or the like. In addition, it is preferable that the first table T1 is periodically updated by the information processing unit 12E. This is because a more reliable table can be obtained by creating the first table T1 using the analysis values and the diagnostic tests for each brain area of a larger number of patients. The first table T1 created by an apparatus or a system outside the information output apparatus 1 may be used. In this case, the information processing unit 12E is not necessary.

The display controller 12F generates a display image for displaying, for example, a medical image (at least one brain image of the first brain image B1 or the second brain image B2) or medical information (analysis value obtained by performing analysis for each brain area of the first brain image B1 and second brain image B2, the table T3, and the diagnostic data D1) on the monitor 24 and outputs the generated display image to the monitor 24, and has a function as an output unit.

Figure 17:
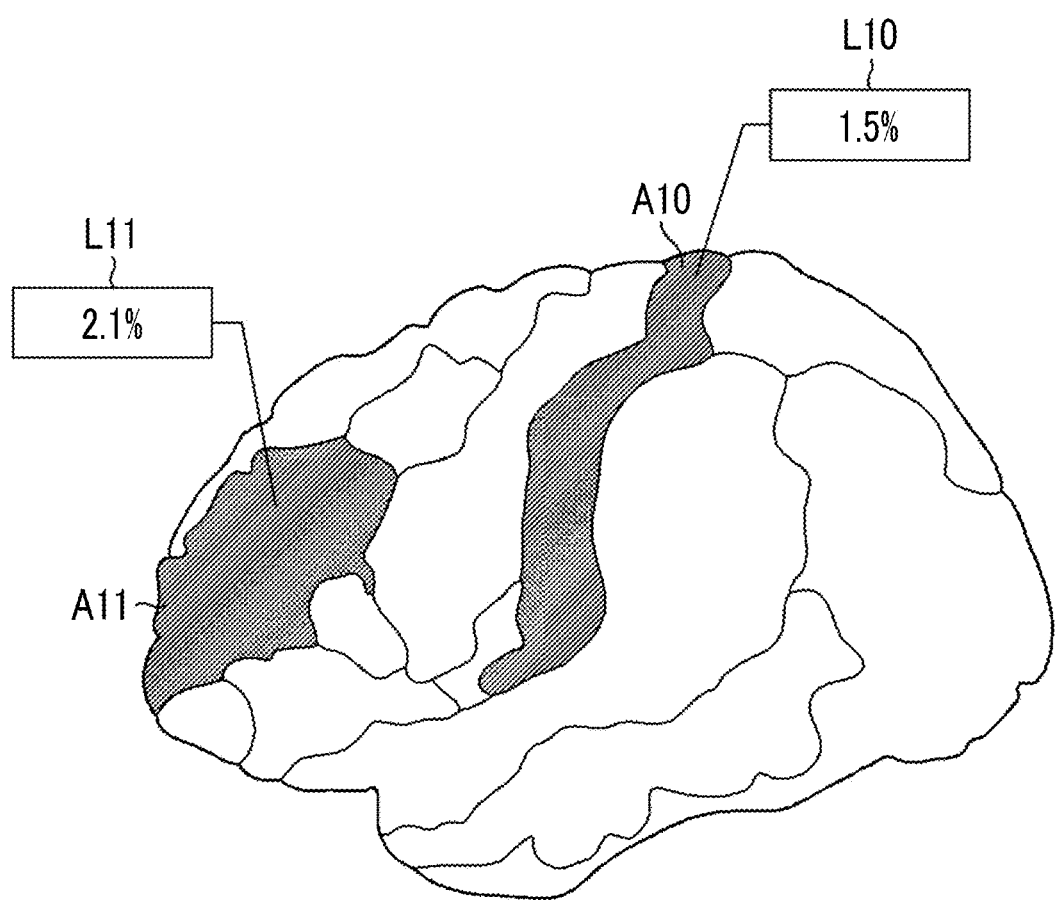
FIG. 17 is a diagram showing an example of a medical image and medical information displayed on a monitor.

FIG. 17 is a diagram showing an example of a medical image and medical information displayed on the monitor 24.

In the example shown in FIG. 17, brain areas A10 and A11 having large atrophy rates (brain areas where the atrophy rate exceeds a threshold value) are displayed so as to be distinguishable from other brain areas as indicated by hatching. For example, by giving a red color to the brain areas A10 and A11, the brain areas A10 and A11 can be displayed so as to be distinguishable from other brain areas by different colors. In addition, labels L10 and L11 can be given to the brain areas A10 and A11. As the labels L10 and L11, analysis values (in the example shown in FIG. 17, an atrophy rate expressed as a percentage) are given. In addition, numbers (Broadmann field: 1 to 52) indicating the brain areas A10 and A11, the name of the brain area, or the like may be displayed.

The display controller 12F can display necessary medical images and medical information on the monitor 24 according to the operation of the operation unit 22 by the doctor.

Next, a table (second table T2 (FIG. 19)) that stores the relevance between a medicine (medicine information indicating a medicine) used for the treatment of dementia and a brain area (one or more brain areas) having significance for the medicine will be described.

The information processing unit 12E has a function of creating the above-described second table T2, and the created second table T2 is stored in the storage 16 and is appropriately used as necessary by the display controller 12F.

In this example, medicines used for the treatment of dementia include an unapproved medicine and an approved medicine. In Japan, clinical trials for unapproved medicines are divided into three phases. Each time the phase goes up, the number of patients is increased and the test is performed to determine safety, effectiveness, and usage.

Figure 18:
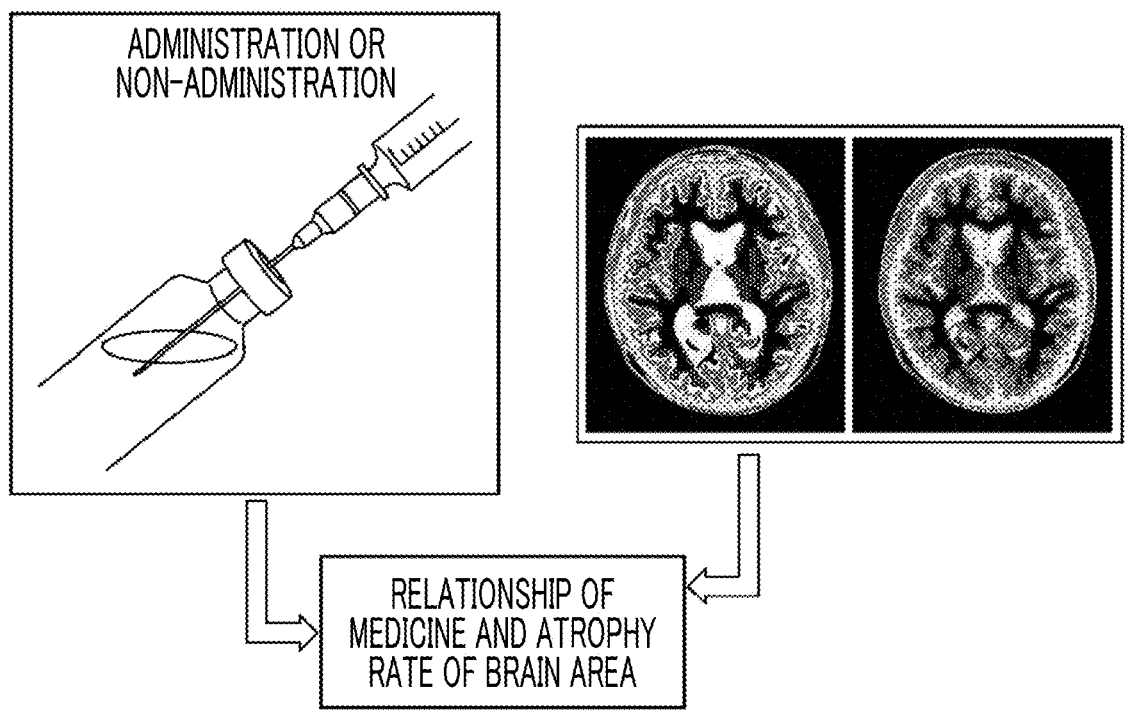
FIG. 18 is a diagram used to describe the relationship between a medicine used for the treatment of dementia and the analysis value of a brain area.

In the first-stage clinical trial for an unapproved medicine (hereinafter, simply referred to as a "medicine"), small-scale (small number of people) clinical trial data is collected. As shown in FIG. 18, a medicine or a placebo is administered to a small number of patients. Then, the analysis value (in this example, the atrophy rate) for each brain area of the brain of a patient to whom a medicine has been administered and the atrophy rate of each brain area of the brain of a patient to whom a placebo has been administered (a patient to whom no medicine has been administered) are collected, and the relevance between the medicine and the atrophy rate of each brain area is calculated.

Specifically, in creating the second table T2, the information processing unit 12E acquires the atrophy rate of each brain area of the brain of a patient, to whom a medicine has been administered, and the atrophy rate of each brain area of the brain of a patient, to whom no medicine has been administered, from the image analysis unit 12D. Information indicating whether the patient is a patient to whom a medicine has been administered or a patient to whom no medicine has been administered can be included in the patient information, and can be acquired from the electronic medical record 3, for example.

The information processing unit 12E compares the statistical amount (for example, an average value) of the atrophy rate of each brain area of the brain of the patient, to whom a medicine has been administered, with the statistical amount of the atrophy rate of each brain area of the brain of the patient, to whom no medicine has been administered, for each brain area, and determines whether or not there is a significant difference in the statistical amount for each brain area. Here, the significant difference means a difference in a case where administration or non-administration of a medicine causes a definite difference in the atrophy rate of the brain area.

In a certain brain area, in a case where the atrophy rate in the case of administration is clearly lower than that in the case of non-administration, it can be considered that the atrophy rate of the brain area is reduced by the administration (there is "significance").

The information processing unit 12E calculates the relevance between the medicine and the brain area having significance for the medicine as described above, and creates the second table T2 that stores the relevance between medicine information indicating the medicine and one or more brain areas among a plurality of brain areas having significance for the medicine.

Figure 19:
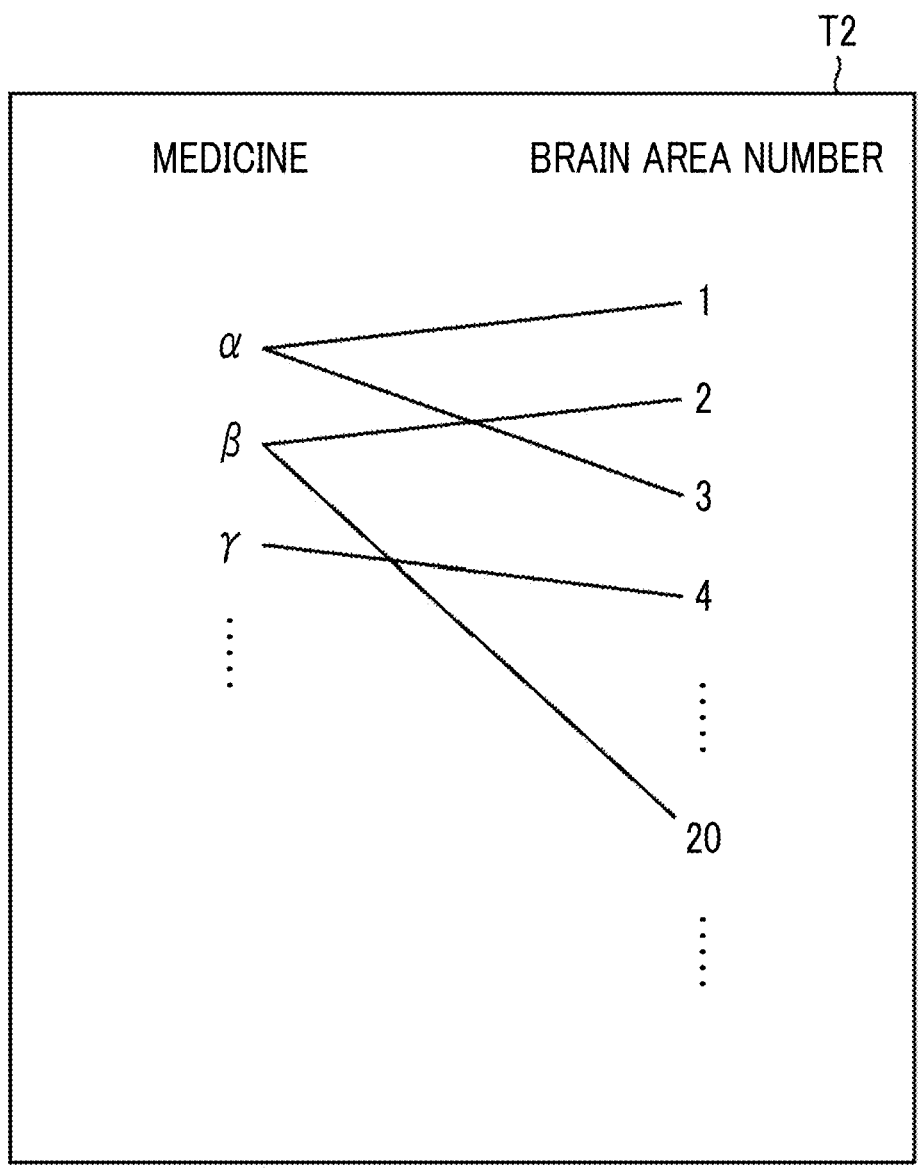
FIG. 19 is a diagram schematically showing a second table T2.

FIG. 19 is a diagram schematically showing the second table T2.

In FIG. 19, α, β, γ, . . . indicate medicines (medicine information such as medicine names), 1, 2, 3, . . . indicate brain areas (for example, brain area numbers according to the Broadmann's brain map), and a medicine and a brain area relevant to each other are connected by a straight line.

For example, in FIG. 19, the medicine a has significance for the brain areas of the brain area numbers 1 and 3 (reduces the atrophy rates of the brain areas of the brain area numbers 1 and 3).

Also in the case of an approved medicine, it is needless to say that the relevance between the approved medicine and one or more brain areas having significance for the approved medicine can be calculated.

Next, a method of using the first table T1 shown in FIG. 16 and the second table T2 shown in FIG. 19 will be described.

<First Usage Example of the First Table T1>

In the first usage example, in a case where a specific brain area among a plurality of brain areas is input by the operation unit 22 that functions as an input unit, the information processing unit 12E or the display controller 12F that functions as an output unit outputs the relevance of a plurality of test items (in this example, the relevance of each item of the eleven items) corresponding to the input brain area (brain area number indicating the brain area) to a subsequent processing unit inside the information processing unit 12E or the display controller 12F or to other processing units that require information of the relevance of each test item to the specific brain area using the first table T1.

For example, in the case of the first table T1 shown in FIG. 16, in a case where a brain area (brain area number 20) is input, the relevance ($A_{20,1}, A_{20,2}, \ldots, A_{20,11}$) of each of the eleven test items is output.

In a processing unit to which the relevance of each of the eleven test items is input, it is possible to specify one or more test items having a relevance exceeding a threshold value (for example, correlation value=0.30) among the relevances of the eleven test items.

The output unit is not limited to outputting the relevance of each of the eleven test items, and one or more test items having a relevance exceeding a threshold value (for example, correlation value=0.30) among the relevances of the eleven test items may be specified and then the specified test items may be output.

According to this, for example, in a case where a brain area of interest, such as a brain area with a high atrophy rate, is input in image diagnosis, a test item having a relevance (high correlation) to the input brain area can be seen.

<Second Usage Example of the First Table T1>

In the first usage example, in a case where a brain area is input, a test item having a relevance to the brain area is output. However, a second usage example is different from the first usage example in that, in a case where a test item is input, a brain area having a relevance to the test item is output.

That is, in a case where a specific test item among a plurality of test items is input by the operation unit 22 that functions as an input unit, the information processing unit 12E or the display controller 12F that functions as an output unit outputs the relevance of a plurality of brain areas (in this example, the relevance of Broadmann field: 1 to 52) corresponding to the input test item (item number indicating the test item) to a subsequent processing unit inside the information processing unit 12E or the display controller 12F or to other processing units that require information of the relevance of each test item to the specific brain area using the table T1.

For example, in the case of the first table T1 shown in FIG. 16, in a case where a test item (item number 1) is input, the relevance ($A_{1,1}, A_{2,1}, \ldots, A_{52,1}$) of each of 52 brain areas is output.

In a processing unit to which the relevance of each of the 52 brain areas is input, it is possible to specify one or more brain areas having a relevance exceeding a threshold value (for example, correlation value=0.30) among the relevances of the 52 brain areas.

The output unit is not limited to outputting the relevance of each of the 52 brain areas, and one or more brain areas having a relevance exceeding a threshold value (for example, correlation value=0.30) among the relevances of the 52 brain areas may be specified and then the specified brain areas may be output.

According to this, for example, in a case where a test item for which the cognitive function has lowered from the test result of the diagnostic test is input, a brain area having a relevance (high correlation) to the input test item can be seen.

<Third Usage Example of the First Table T1 and the Second Table T2>

In the third usage example, in a case where medicine information indicating a specific medicine used for the treatment of dementia is input by the operation unit 22 that functions as an input unit, the information processing unit 12E or the display controller 12F that functions as an output unit specifies a brain area having significance for the specific medicine based on the input medicine information of the specific medicine and the second table T2 (FIG. 19), specifies a test item having a relevance exceeding a threshold value (for example, correlation value=0.30) for the specified brain area based on the specified brain area and the first table T1, and outputs the specified test item to a subsequent processing unit inside the information processing unit 12E or the display controller 12F or to other processing units that require information of the test item highly relevant to the medicine.

For example, in the case of the second table T2 shown in FIG. 19, in a case where a specific medicine a is input, brain areas (brain area numbers 1 and 3) having significance for the medicine a are specified by the second table T2.

In a case where the brain areas (brain area numbers 1 and 3) having significance for the medicine a are specified using the second table T2, a test item highly relevant to the specified brain areas (brain area numbers 1 and 3) can be specified based on the specified brain areas (brain area numbers 1 and 3) and the first table T1.

According to this, in a case where medicine information indicating a medicine used for the treatment of dementia is input, a test item for which the effect of the medicine corresponding to the medicine information can be expected (that is, for which cognitive function the medicine is effective) can be seen.

In the first-stage small-scale clinical trial for an unapproved medicine, test items for which the effect of the unapproved medicine can be expected can be predicted to some extent. Using the predicted test items, it is possible to easily determine target patients for the second-stage medium-scale clinical trial and the third-stage large-scale clinical trial. Therefore, it is possible to reduce the burden on patients who do not require clinical trials obviously. In this manner, it is possible to improve the quality of clinical trials.

<Fourth Usage Example of the First Table T1 and the Second Table T2>

In the third use example, in a case where medicine information is input, a test item for which the effect of the medicine corresponding to the medicine information can be expected is output. However, a fourth usage example is different from the third usage example in that, in a case where a test item of interest is input, medicine information that can be expected to have an effect on the cognitive function indicated by the test item is output.

That is, in a case where a test item of interest is input by the operation unit 22 that functions as an input unit, the information processing unit 12E or the display controller 12F that functions as an output unit specifies one or more brain areas having a relevance exceeding a threshold value (for example, correlation value=0.30) among the plurality of brain areas based on the input test item and the first table T1. Then, one or more medicines, which have significance for the specified brain area and are used for the treatment of dementia, are specified based on the specified brain area and the second table (FIG. 19), and medicine information indicating the specified medicine is output to a subsequent processing unit inside the information processing unit 12E or the display controller 12F or to other processing units that require the medicine information.

According to this, from the test result of the dementia diagnostic test for the patient, the medicine information of one or more medicines suitable for the treatment of the patient can be acquired. Therefore, it is possible to support the selection of the medicine by the doctor.

[Information Output Method]

First Embodiment of an Information Output Method

Figure 20:
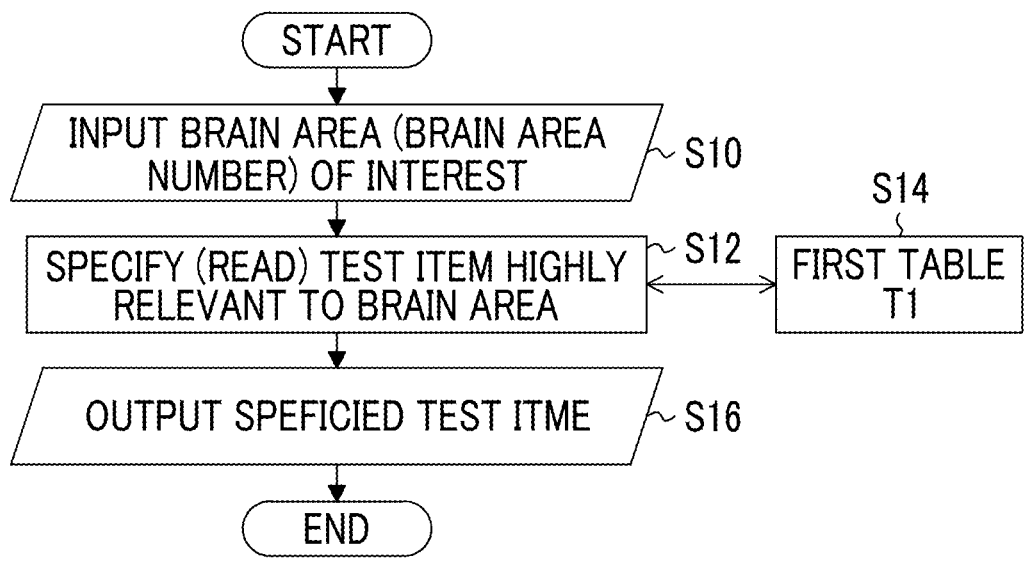
FIG. 20 is a flowchart showing a first embodiment of an information output method according to the present invention.

FIG. 20 is a flowchart showing a first embodiment of an information output method according to the present invention.

In FIG. 20, the information output apparatus 1 shown in FIG. 1 receives an input of a brain area of interest using the operation unit 22, such as a mouse and a keyboard, and the monitor 24 (step S10). In the example shown in FIG. 17, the brain areas A10 and A11 having large atrophy rates are displayed on the monitor 24 so as to be distinguishable from other brain areas as indicated by hatching. The doctor can determine, for example, a brain area (in FIG. 17, the brain area A10 or A11) having a high atrophy rate as a brain area of interest while observing the monitor 24, and input the brain area of interest (brain area number indicating the brain area) by an operation using the operation unit 22.

The information processing unit 12E or the display controller 12F that functions as an output unit of the information output apparatus 1 specifies and reads a test item highly relevant to the received brain area (one or more test items having a relevance exceeding a threshold value among the plurality of test items) based on the brain area (brain area number indicating the brain area) received in step S10 using the first table T1 (step S14, FIG. 16) prepared in advance in the storage 16 (step S12). Then, the test item specified in step S12 is output (step S16).

As described above, in a case where the input of the brain area of interest is received, the display controller 12F can display a test item highly relevant to the brain area on the monitor 24. Therefore, it is possible to provide information effective for the diagnosis of dementia. For example, in a case where the doctor inputs a brain area having a high atrophy rate of a certain patient as a brain area of interest, which test item the brain area of interest affects (that is, which cognitive function is lowered) can be predicted from test items highly relevant to the brain area of interest without performing a dementia diagnostic test for the patient. In addition, in a case where the doctor performs a dementia diagnostic test for the patient, it is possible to compare actual test results with test items highly relevant to the brain area having a high atrophy rate. This can be used for diagnosis of dementia and evaluation of a treatment method or a diagnostic method.

In the first embodiment described above, in a case where the input of a brain area of interest is received, a test item highly relevant to the brain area is output. However, the information processing unit 12E that functions as an output unit may read the relevance of a plurality of test items (in this example, all eleven items of ADAS) corresponding to the brain area from the first table T1 based on the received brain area and the first table T1 and output the read relevance.

Due to the output relevance of a plurality of test items, for example, it is possible to extract a test item exceeding the threshold value or to sort the plurality of test items in descending order of the relevance and extract a plurality of high-order test items. Such information can be used for diagnosis of dementia.

Second Embodiment of an Information Output Method

Figure 21:
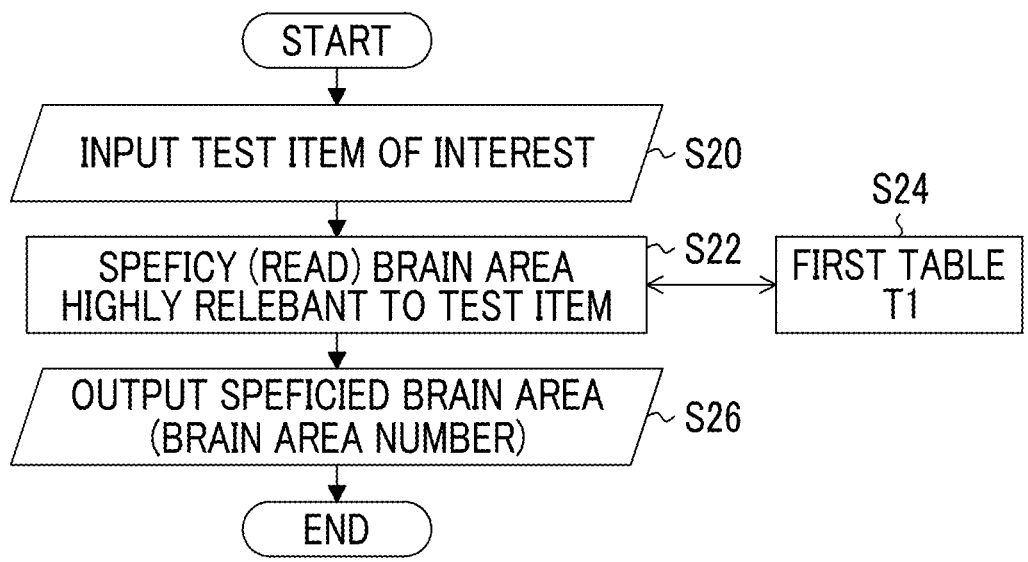
FIG. 21 is a flowchart showing a second embodiment of the information output method according to the present invention.

FIG. 21 is a flowchart showing a second embodiment of the information output method according to the present invention.

In the information output method of the first embodiment, in a case where the input of a brain area is received, a test item having a relevance to the brain area is output. In contrast to the information output method of the first embodiment, in the information output method of the second embodiment, in a case where the input of a test item is input, a brain area having a relevance to the test item is output. This is the different point from the first embodiment.

In FIG. 21, the information output apparatus 1 shown in FIG. 1 receives an input of a test item of interest using the operation unit 22 and the monitor 24 (step S20). For example, in a case where there is a test item whose score is greatly reduced compared with the previous test result from a test result obtained by performing a dementia diagnostic test for a certain patient, the doctor can determine the test item whose score is greatly reduced as a test item of interest and input the test item of interest by an operation using the operation unit 22.

The information processing unit 12E or the display controller 12F that functions as an output unit specifies and reads a brain area highly relevant to the received test item (one or more brain areas having a relevance exceeding a threshold value among the plurality of brain areas) based on the test item received in step S20 using the first table T1 (step S24) prepared in advance in the storage 16 (step S22). Then, the brain area (brain area number or name indicating the brain area) specified in step S22 is output (step S26).

As described above, in a case where the input of the test item of interest is received, the display controller 12F can display a brain area highly relevant to the test item on the monitor 24. Therefore, it is possible to provide information effective for the diagnosis of dementia. For example, in a case where the doctor inputs a test item whose score is greatly reduced from the dementia test result of a certain patient as a test item of interest, a brain area highly relevant to the test item of interest can be seen. Therefore, the doctor can make image diagnosis of brain images focusing on the atrophy rate and the like of the brain area highly relevant to the test item of interest. This can be used for diagnosis of dementia and evaluation of a treatment method or a diagnostic method.

In the second embodiment described above, in a case where the input of a test item of interest is received, a brain area highly relevant to the test item is output. However, the information processing unit 12E that functions as an output unit may read the relevance of a plurality of brain areas (in this example, brain areas of 1 to 52) corresponding to the test item from the first table T1 based on the received test item and the first table T1 and output the read relevance.

Due to the output relevance of a plurality of brain areas, for example, it is possible to extract a brain area exceeding the threshold value or to sort the plurality of brain areas in descending order of the relevance and extract a plurality of high-order brain areas. Such information can be used for diagnosis of dementia.

Third Embodiment of an Information Output Method

Figure 22:
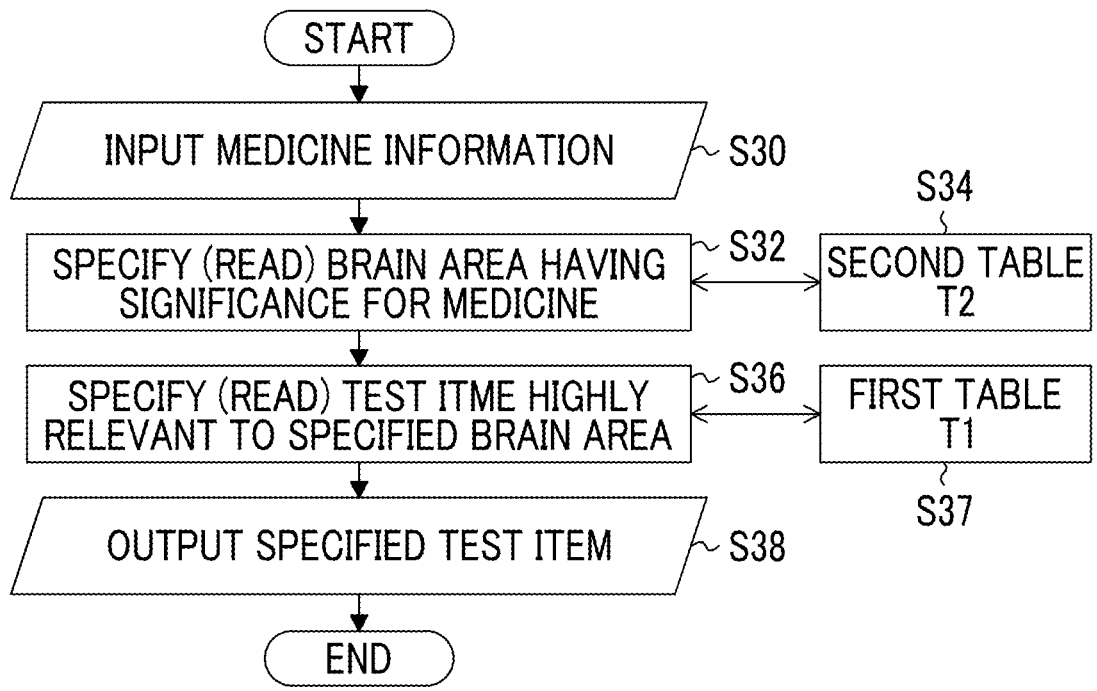
FIG. 22 is a flowchart showing a third embodiment of the information output method according to the present invention.

FIG. 22 is a flowchart showing a third embodiment of the information output method according to the present invention.

In FIG. 22, the information output apparatus 1 shown in FIG. 1 receives an input of medicine information indicating a medicine used for the treatment of dementia using the operation unit 22 and the monitor 24 (step S30). As the medicine information, any medicine information of an approved medicine or an unapproved medicine may be used.

The information processing unit 12E or the display controller 12F that functions as an output unit of the information output apparatus 1 specifies and reads a brain area having significance for the medicine corresponding to the medicine information (for example, a brain area whose atrophy rate is reduced by medicine administration) based on the medicine information received in step S30 and the second table T2 using the second table T2 (step S34, FIG. 19) prepared in advance in the storage 16 (step S32).

Then, using the first table T1 (step S37) prepared in advance in the storage 16, one or more test items (test items highly relevant to the specified brain area) among the plurality of test items are specified and read with respect to the brain area specified in step S32 and the brain area specified based on the first table T1 (step S36). Then, the test item specified in step S36 is output (step S38). The test item highly relevant to the specified brain area can be, for example, a test item having a relevance exceeding a threshold value with respect to the specified brain area or one or more test items having a high-order relevance obtained by sorting the relevances of a plurality of test items corresponding to the specified brain area in descending order of the relevance.

As described above, in a case where the medicine information indicating the specific medicine used for the treatment of dementia is input, a brain area having significance for the medicine corresponding to the medicine information can be specified using the first table T1 and the second table T2, and a test item highly relevant to the specified brain area among the plurality of test items of the dementia diagnostic test can be specified and output. That is, by inputting the medicine information indicating the medicine used for the treatment of dementia, a test item for which the effect of the medicine corresponding to the medicine information can be expected (for which cognitive function the medicine is effective) can be seen.

In addition, target patients for clinical trials for checking the effects or side effects of medicines can be easily determined using the test results of diagnostic tests that can be expected to be effective. Therefore, it is possible to reduce the burden on patients who do not require clinical trials obviously. In this manner, it is possible to improve the quality of clinical trials.

Fourth Embodiment of an Information Output Method

Figure 23:
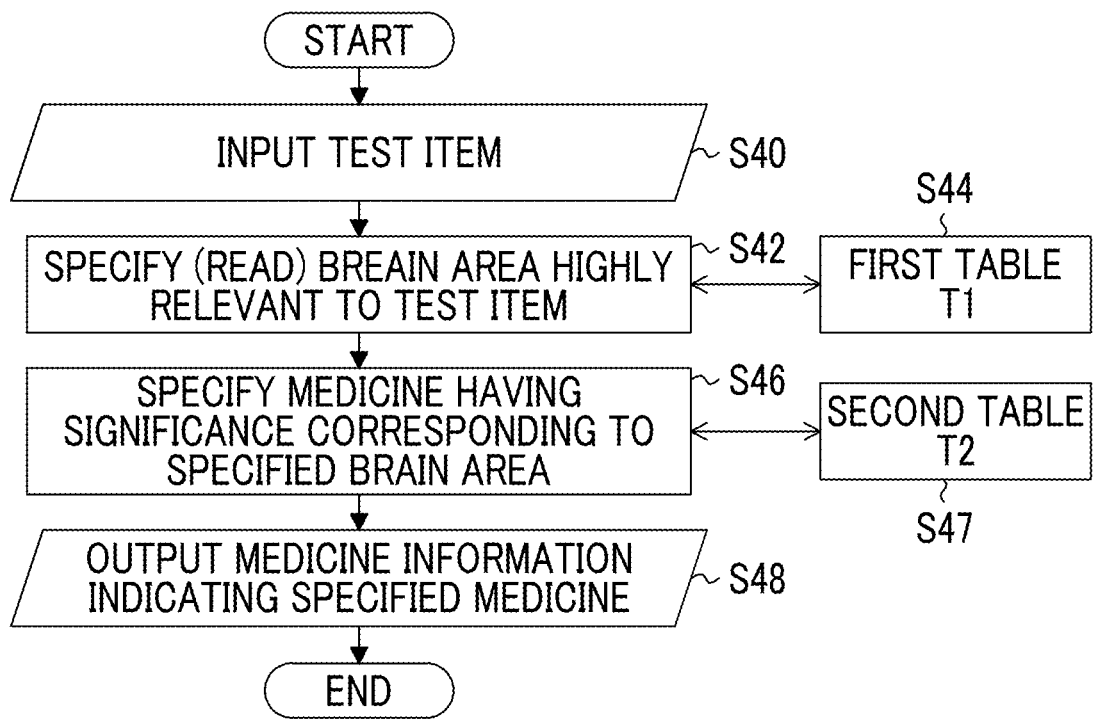
FIG. 23 is a flowchart showing a fourth embodiment of the information output method according to the present invention.

FIG. 23 is a flowchart showing a fourth embodiment of the information output method according to the present invention.

In the information output method of the third embodiment, in a case where the input of medicine information is received, a test item for which the effect of the medicine corresponding to the medicine information can be expected is output. In contrast to the information output method of the third embodiment, in the information output method of the fourth embodiment, in a case where the input of a test result is input, medicine information indicating a medicine that can be expected to improve the cognitive function indicated by the test result is output. This is the different point from the third embodiment.

In FIG. 23, the information output apparatus 1 shown in FIG. 1 receives an input of a test result (test item of interest) using the operation unit 22 and the monitor 24 (step S40). For example, in a case where there is a test item whose score is greatly reduced compared with the previous test result from a test result obtained by performing a dementia diagnostic test for a certain patient, the doctor can determine the test item whose score is greatly reduced as a test item of interest and input the test item of interest (test result) by an operation using the operation unit 22.

The information processing unit 12E or the display controller 12F that functions as an output unit of the information output apparatus 1 specifies and reads one or more brain areas (brain areas highly relevant to the test item of interest), among the plurality of brain areas, based on the test result (test item of interest) received in step S40 and the first table T1 using the first table T1 (step S44) prepared in advance in the storage 16 (step S42).

Then, using the second table T2 (step S47) prepared in advance in the storage 16, one or more medicines that have significance for the specified brain area and are used for the treatment of dementia (for example, medicines that reduce the atrophy rate of the specified brain area) are specified and read based on the brain area specified in step S42 and the second table T2 (step S46). Then, the medicine information indicating the medicine specified in step S46 is output (step S48).

As described above, in a case where the test item of interest is input, a medicine used for the treatment of dementia can be specified using the first table T1 and the second table T2 and medicine information indicating the specified medicine can be output. That is, from the test result of the dementia diagnostic test for the subject (patient), the medicine information of one or more medicines suitable for the treatment of the patient can be acquired. Therefore, it is possible to support the selection of the medicine by the doctor.

The first table T1 and the second table T2 used in the third embodiment and the fourth embodiment are not limited to two tables, and may be integrated into one table using a brain area common to the first table T1 and the second table T2, for example.

[Additional Remark]

The information output apparatus 1 of the present embodiment is merely an example, and the present invention can be applied to other configurations. Each functional configuration can be appropriately realized by certain hardware, software, or a combination of both. For example, the present invention can also be applied to an information output program causing a computer to execute processing in each unit of the information output apparatus 1 described above and a computer-readable recording medium (non-transitory recording medium) that records such an information output program.

In the present embodiment, for example, the hardware structures of processing units for executing various kinds of processing, such as the image acquisition unit 12A, the data acquisition unit 12B, the brain area division unit 12C, the image analysis unit 12D, the information processing unit 12E, and the display controller 12F, are various processors shown below. The various processors include a central processing unit (CPU) that is a general-purpose processor that executes software (program) to function as various processing units, a programmable logic device (PLD) that is a processor whose circuit configuration can be changed after manufacture, such as a field programmable gate array (FPGA), and a dedicated electric circuit that is a processor having a circuit configuration that is designed for exclusive use in order to execute specific processing, such as an application specific integrated circuit (ASIC).

One processing unit may be configured by one of these various processors, or may be configured by two or more processors of the same type or different types (for example, a plurality of FPGAs or a combination of a CPU and an FPGA). Alternatively, a plurality of processing units may be configured by one processor. As an example of configuring a plurality of processing units using one processor, first, as represented by a computer, such as a client or a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. Thus, various processing units are configured by using one or more of the above-described various processors as a hardware structure.

In addition, the hardware structure of these various processors is an electrical circuit (circuitry) in the form of a combination of circuit elements, such as semiconductor elements.

The present invention is an information output apparatus having a processor. The processor uses a first table that stores the relevance between a plurality of divided brain areas of a brain image and a plurality of test items of a dementia diagnostic test, and includes an information output apparatus that receives brain areas and reads and outputs the relevance of a plurality of test items corresponding to the brain areas or one or more test items, which have relevance exceeding a threshold value among the plurality of test items, from the first table based on the received brain areas and the first table. Alternatively, the processor uses the above-described first table, and includes an information output apparatus that receives test items and reads and outputs the relevance of a plurality of brain areas corresponding to the test items or one or more brain areas, which have relevance exceeding a threshold value among the plurality of brain areas, from the first table based on the received test items and the first table.

It is needless to say that the present invention is not limited to the above-described embodiments and various modifications can be made without departing from the spirit of the present invention.

EXPLANATION OF REFERENCES

1: information output apparatus
2: PACS
3: electronic medical record
4: MRI apparatus
10: computer
12: CPU
12A: image acquisition unit
12B: data acquisition unit
12C: brain area division unit
12D: image analysis unit
12E: information processing unit
12F: display controller
14: main memory
16: storage
18: optical disc drive
20: communication interface
22: operation unit
24: monitor
A10, A11: brain area
B1: first brain image
B2: second brain image
Bs: standard brain image
D1: diagnostic data
L10, L11: label
S10 to S48: step
T1: first table
T2: second table
T3: table

What is claimed is:

1. An information output apparatus, comprising:
a first table that stores relevance, which is correlation values, between a plurality of divided brain areas of a brain image captured by a magnetic resonance imaging (MRI) apparatus and a plurality of test items of a dementia diagnostic test, wherein the correlation value is relevance between a score and atrophy rate of the test items, and the plurality of divided brain areas are brain areas divided corresponding to a Broadmann's brain map;
at least one of processor configured to:
input at least one specific brain area; and
read and selectively output the correlation values of the plurality of test items of the dementia diagnostic test with respect to the specific brain area or one or more test items of the dementia diagnostic test that has correlation value exceeding a threshold value among the plurality of test items of the dementia diagnostic test, from the first table based on the specific brain area.

2. An information output apparatus, comprising:
a first table that stores relevance, which is correlation values, between a plurality of divided brain areas of a brain image captured by a magnetic resonance imaging (MRI) apparatus and a plurality of test items of a dementia diagnostic test, wherein the correlation value is relevance between a score and atrophy rate of the test items, and the plurality of divided brain areas are brain areas divided corresponding to a Broadmann's brain map;

at least one of processor configured to:

input the test items of the dementia diagnostic test; and read and output the correlation values of the plurality of brain areas with respect to the test items of the dementia diagnostic test or one or more brain areas that has correlation values exceeding a threshold value among the plurality of brain areas, from the first table based on the input test items of the dementia diagnostic test.

3. An information output method, comprising:

a step of preparing a first table that stores relevance, which is correlation values, between a plurality of divided brain areas of a brain image captured by a magnetic resonance imaging (MRI) apparatus and a plurality of test items of a dementia diagnostic test, wherein the correlation value is relevance between a score and atrophy rate of the test items, and the plurality of divided brain areas are brain areas divided corresponding to a Broadmann's brain map;

a step of receiving an input of at least one specific brain area; and a step of reading and selectively outputting correlation values of the plurality of test items of the dementia diagnostic test with respect to the specific brain area or one or more test items of the dementia diagnostic test that has correlation value relevance exceeding a threshold value among the plurality of test items of the dementia diagnostic test, from the first table based on the received at least one brain area.

4. An information output method, comprising:

a step of preparing a first table that stores relevance, which is correlation values, between a plurality of divided brain areas of a brain image captured by a magnetic resonance imaging (MRI) apparatus and a plurality of test items of a dementia diagnostic test, wherein the correlation value is relevance between a score and atrophy rate of the test items, and the plurality of divided brain areas are brain areas divided corresponding to a Broadmann's brain map;

a step of receiving an input of the test items of the dementia diagnostic test; and a step of reading and outputting correlation values of the plurality of brain areas with respect to the test items of the dementia diagnostic test or one or more brain areas that has correlation value relevance exceeding a threshold value among the plurality of brain areas, from the first table based on the received test items of the dementia diagnostic test.

5. A non-transitory computer readable recording medium storing an information output program applied to a computer comprising a first table that stores relevance, which is correlation values, between a plurality of divided brain areas of a brain image captured by a magnetic resonance imaging (MRI) apparatus and a plurality of test items of a dementia diagnostic test, wherein the correlation value is relevance between a score and atrophy rate of the test items, and the plurality of divided brain areas are brain areas divided corresponding to a Broadmann's brain map; the program causing the computer to:

receive an input of at least one specific brain area; and read and selectively output the correlation values of the plurality of test items of the dementia diagnostic test with respect to the specific brain area or one or more test items of the dementia diagnostic test that has correlation value exceeding a threshold value among the plurality of test items of the dementia diagnostic test, from the first table based on the received specific brain areas.

6. A non-transitory computer readable recording medium storing an information output program applied to a computer comprising a first table that stores relevance, which is correlation values, between a plurality of divided brain areas of a brain image captured by a magnetic resonance imaging (MRI) apparatus and a plurality of test items of a dementia diagnostic test, wherein the correlation value is relevance between a score and atrophy rate of the test items, and the plurality of divided brain areas are brain areas divided corresponding to a Broadmann's brain map;

the program causing the computer to:

receive an input of the test items of the dementia diagnostic test; and read and output correlation values of the plurality of brain areas with respect to the test items of the dementia diagnostic test or one or more brain areas that has correlation value exceeding a threshold value among the plurality of brain areas, from the first table based on the received test items of the dementia diagnostic test.

\* \* \* \* \*